United States Patent
Munro

(10) Patent No.: US 9,476,825 B2
(45) Date of Patent: Oct. 25, 2016

(54) OPTICAL IMAGING SYSTEM WITH MULTIPLE IMAGING CHANNEL OPTICAL SENSING

(71) Applicants: Baxter Healthcare SA, Glattpark (Opfikon) (CH); Baxter International Inc., Deerfield, IL (US)

(72) Inventor: James F. Munro, Ontario, NY (US)

(73) Assignees: BAXTER INTERNATIONAL INC., Deerfield, IL (US); BAXTER HEALTHCARE S.A., Glattpark(Opfikon) (CH)

(*) Notice: Subject to any disclaimer, the term of this patent is extended or adjusted under 35 U.S.C. 154(b) by 178 days.

(21) Appl. No.: 13/828,744

(22) Filed: Mar. 14, 2013

(65) Prior Publication Data
US 2013/0201482 A1    Aug. 8, 2013

Related U.S. Application Data

(63) Continuation-in-part of application No. 12/907,403, filed on Oct. 19, 2010, now Pat. No. 8,622,979.

(51) Int. Cl.
*A61M 5/14* (2006.01)
*G01N 21/25* (2006.01)
*A61M 5/168* (2006.01)

(52) U.S. Cl.
CPC .......... *G01N 21/255* (2013.01); *A61M 5/1689* (2013.01); *A61M 2205/3306* (2013.01)

(58) Field of Classification Search
CPC ................. A61M 5/1689; A61M 5/1411
USPC ....................................................... 604/251
See application file for complete search history.

(56) References Cited

U.S. PATENT DOCUMENTS

| | | |
|---|---|---|
| 3,609,379 A | 9/1971 | Hildebrandt |
| 4,321,461 A | 3/1982 | Walter, Jr. et al. |
| 4,328,801 A | 5/1982 | Marx et al. |
| 4,504,263 A | 3/1985 | Steuer et al. |
| 4,525,163 A | 6/1985 | Slavik et al. |
| 4,583,975 A | 4/1986 | Pekkarinen et al. |
| 4,634,426 A | 1/1987 | Kamen |

(Continued)

FOREIGN PATENT DOCUMENTS

| | | |
|---|---|---|
| DE | 3617723 | 12/1987 |
| WO | 9309407 | 5/1993 |

(Continued)

*Primary Examiner* — Edelmira Bosques
(74) *Attorney, Agent, or Firm* — Greer, Burns & Crain, Ltd.

(57) ABSTRACT

An optical imaging system for use with an infusion tube including: at least one light source for emitting at least two of first, second, or third spectrums of light; an optics system including a single lens for receiving and transmitting at least two of the first spectrum light transmitted through a first portion of the chamber, the second spectrum light transmitted through a second portion of the chamber, or the third spectrum light transmitted through a third portion of the chamber. The system includes a sensor receiving the at least two of the spectrums from the lens and generating and transmitting data characterizing the at least two of the spectrums. The system includes a memory element storing computer readable instructions and a processor to execute the instructions to generate, using the data, at least two of first, second, or third images of the first, second, and third portions, respectively.

37 Claims, 21 Drawing Sheets

(56) References Cited

U.S. PATENT DOCUMENTS

| | | |
|---|---|---|
| 4,673,820 A | 6/1987 | Kamen |
| 4,680,977 A | 7/1987 | Conero et al. |
| 4,703,314 A | 10/1987 | Spani |
| 4,718,896 A | 1/1988 | Arndt et al. |
| 4,812,904 A * | 3/1989 | Maring et al. ............... 348/135 |
| 4,820,281 A | 4/1989 | Lawler, Jr. |
| 4,909,786 A | 3/1990 | Gijselhart et al. |
| 4,936,828 A | 6/1990 | Chiang |
| 5,045,069 A | 9/1991 | Imparato |
| 5,057,090 A | 10/1991 | Bessman |
| 5,186,057 A | 2/1993 | Everhart |
| 5,267,980 A | 12/1993 | Dirr, Jr. et al. |
| 5,331,309 A | 7/1994 | Sakai |
| 5,411,052 A | 5/1995 | Murray |
| 5,415,641 A | 5/1995 | Yerlikaya et al. |
| 5,526,285 A * | 6/1996 | Campo et al. ............... 356/405 |
| 5,562,615 A | 10/1996 | Nassif |
| 5,588,963 A | 12/1996 | Roelofs |
| 5,899,665 A | 5/1999 | Makino et al. |
| 5,920,361 A * | 7/1999 | Gibeau et al. ............... 348/750 |
| 6,049,381 A | 4/2000 | Reintjes et al. |
| 6,083,206 A | 7/2000 | Molko |
| 6,091,492 A * | 7/2000 | Strickland et al. ......... 356/336 |
| 6,149,631 A | 11/2000 | Haydel, Jr. |
| 6,159,186 A | 12/2000 | Wickham et al. |
| 6,213,354 B1 | 4/2001 | Kay |
| 6,562,012 B1 | 5/2003 | Brown et al. |
| 6,599,282 B2 | 7/2003 | Burko |
| 6,736,801 B1 | 5/2004 | Gallagher |
| 6,984,052 B1 | 1/2006 | Del Castillo |
| 7,190,275 B2 | 3/2007 | Goldberg et al. |
| 7,695,448 B2 | 4/2010 | Cassidy et al. |
| 7,767,991 B2 | 8/2010 | Sacchetti |
| 7,892,204 B2 | 2/2011 | Kraus |
| 7,918,834 B2 | 4/2011 | Mernoe et al. |
| 2001/0055462 A1* | 12/2001 | Seibel .......................... 385/147 |
| 2003/0045840 A1 | 3/2003 | Burko |
| 2006/0291211 A1 | 12/2006 | Rodriguez et al. |
| 2007/0102623 A1* | 5/2007 | Fengler et al. ............ 250/208.1 |
| 2008/0004574 A1 | 1/2008 | Dyar et al. |
| 2008/0051732 A1 | 2/2008 | Chen |
| 2009/0097029 A1 | 4/2009 | Tokhtuev et al. |
| 2009/0262351 A1 | 10/2009 | Erickson et al. |
| 2010/0309005 A1 | 12/2010 | Warner et al. |
| 2011/0025826 A1* | 2/2011 | Dabiri ...................... G01P 5/20 348/47 |
| 2011/0046899 A1 | 2/2011 | Paz |
| 2011/0190637 A1* | 8/2011 | Knobel .............. A61B 19/5244 600/476 |
| 2012/0013735 A1 | 1/2012 | Tao |
| 2012/0095433 A1 | 4/2012 | Hungerford et al. |

FOREIGN PATENT DOCUMENTS

| | | | |
|---|---|---|---|
| WO | 02/40084 | 5/2002 | |
| WO | 2009039203 | 3/2009 | |
| WO | WO 2010020397 A1 * | 2/2010 | ......... A61B 19/5244 |

* cited by examiner

COLLIMATED ILLUMINATION

DIFFUSE ILLUMINATION

TELECENTRIC IMAGING

STRUCTURED ILLUMINATION

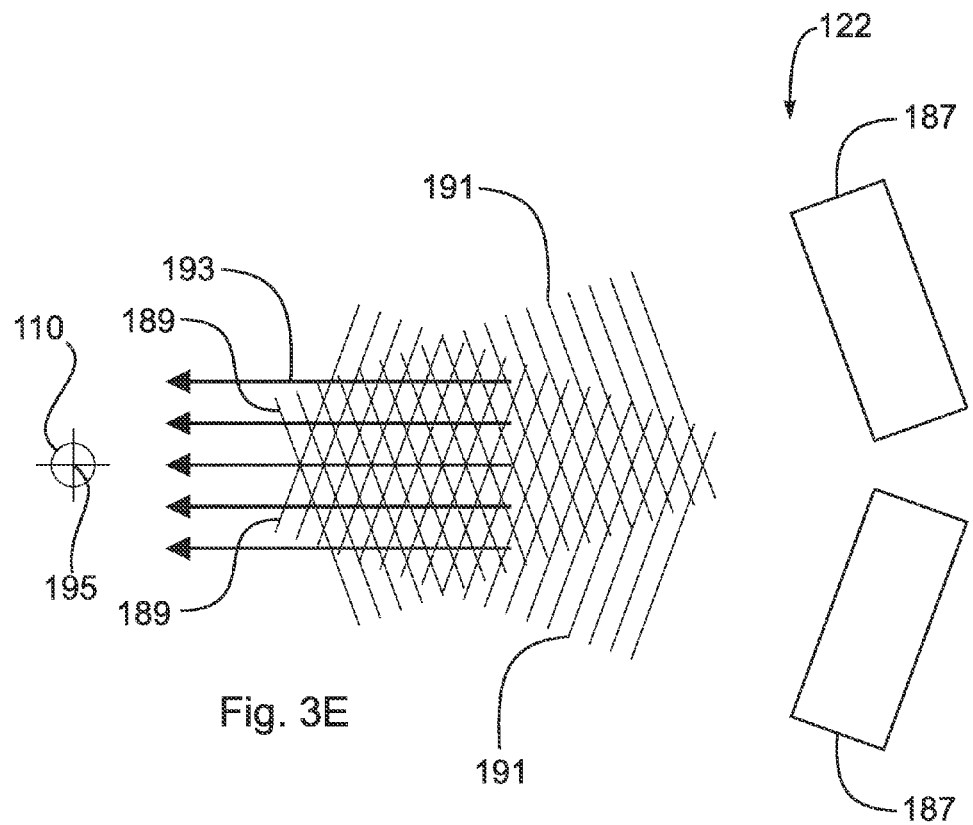
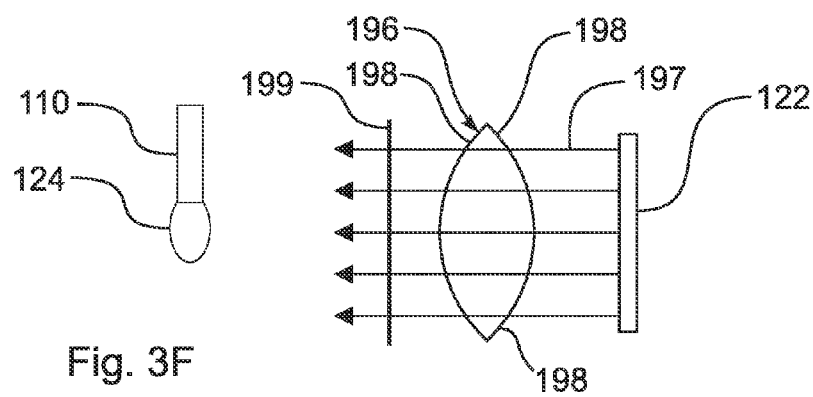

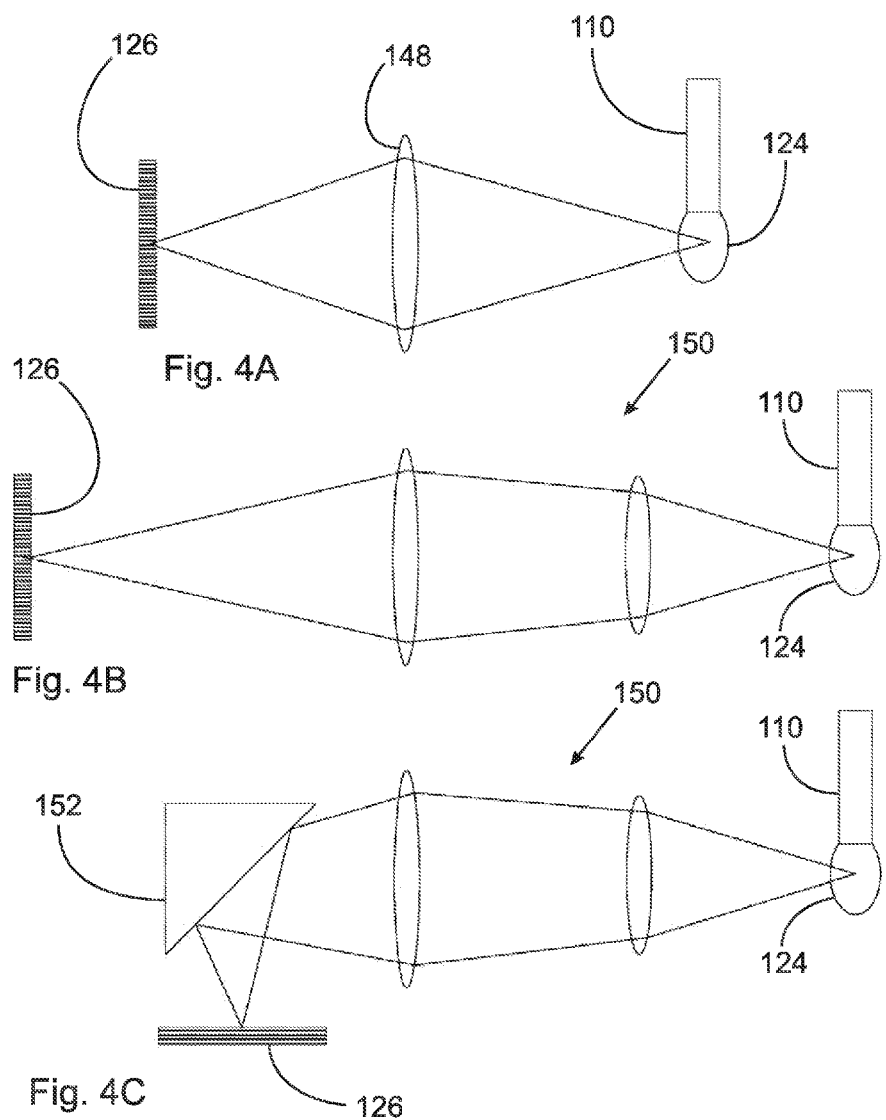

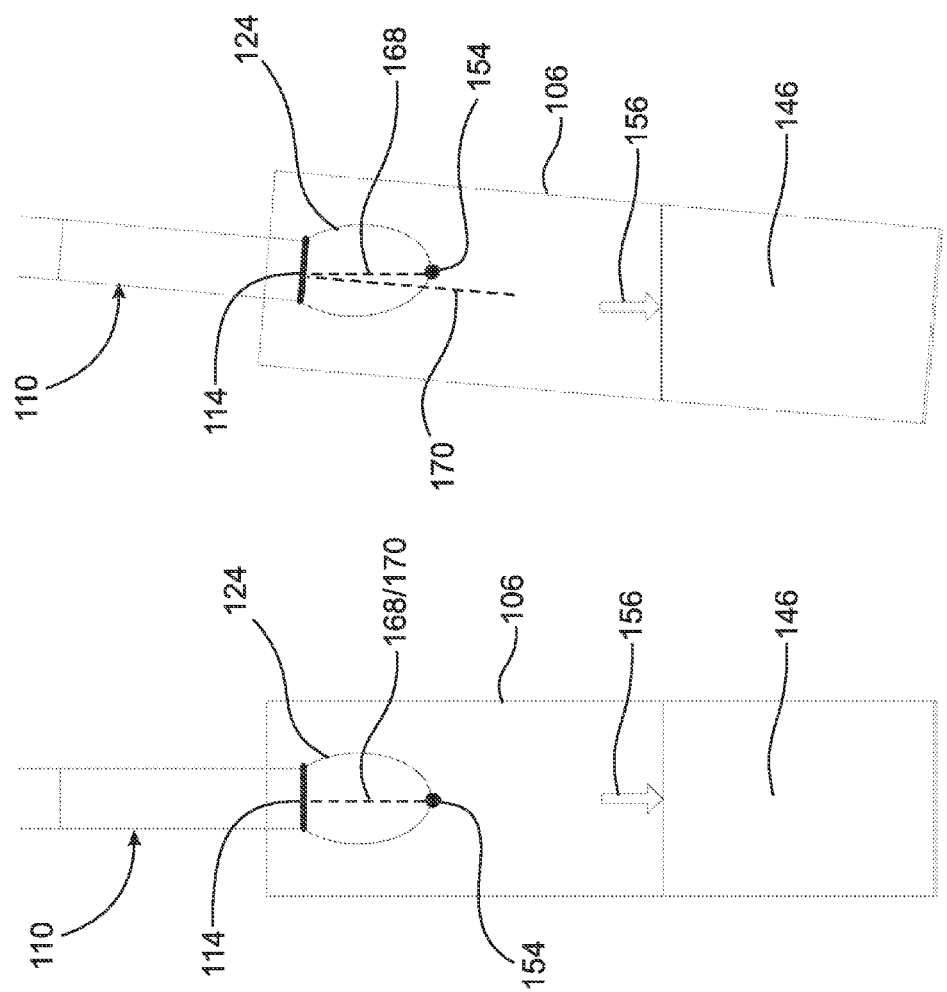

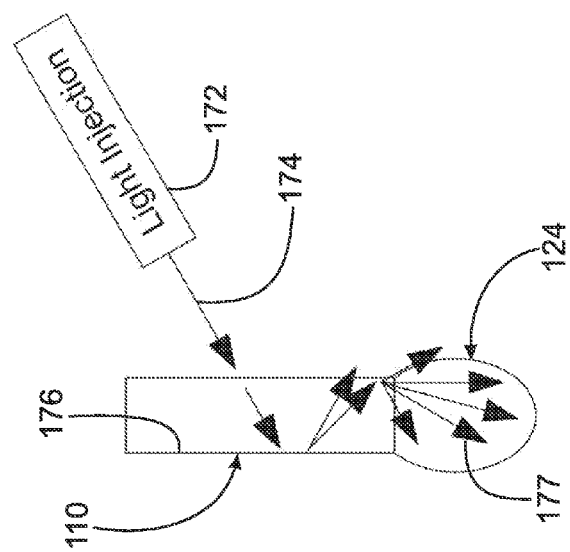
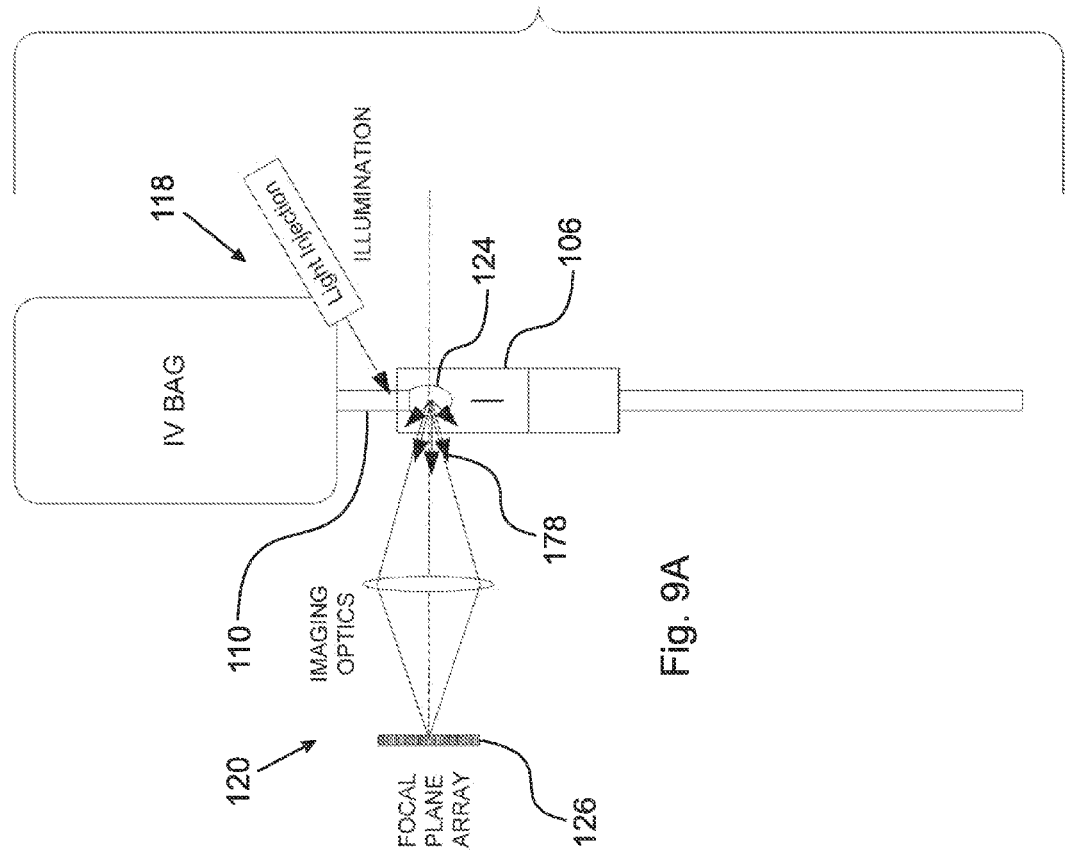
Fig. 9B
Fig. 9A

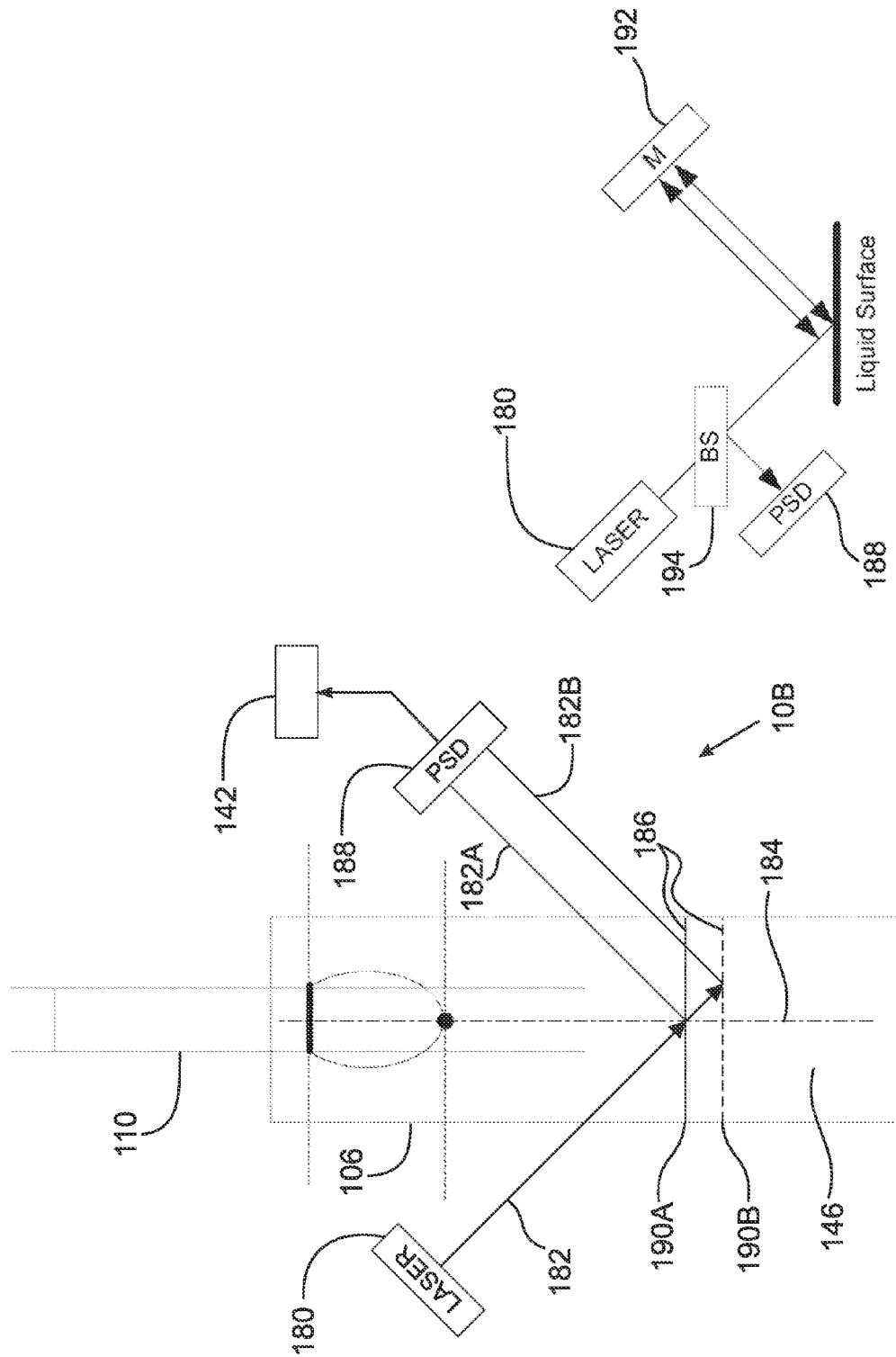

OPTICAL IMAGING SYSTEM WITH MULTIPLE IMAGING CHANNEL OPTICAL SENSING

CROSS REFERENCE TO RELATED APPLICATIONS

This is a continuation-in-part patent application under 35 USC 120 of U.S. patent application Ser. No. 12/907,403 filed Oct. 19, 2010, which application is incorporated herein by reference.

TECHNICAL FIELD

The present disclosure relates generally to an infusion pump with chromatic multiplexing, in particular, the pump uses single or multiple light sources, a single lens, mirrors, and beam combiners to enable use of a single color image sensor to provide distinct images for multiple distinct portions of the pump.

BACKGROUND

Monochrome image sensors are generally less costly than color image sensors. However, for simultaneously received multiple images, monochrome sensors cannot be used to separate the respective images, for example to generate, display, or operate upon the respective images, using conventional signal processing. For example, when a pixel in the monochrome sensor receives light, the sensor cannot determine which of the respective images the light pertains to.

SUMMARY

According to aspects illustrated herein, there is provided an optical imaging system for use with an infusion tube having a drip chamber including a first portion with a drip tube, a second portion with an exit port, and a third portion located between the first and second portions, the optical imaging system including: at least one light source for emitting at least two of first, second, or third spectrums of light; an optics system including a single lens for receiving and transmitting at least two of the first spectrum of light transmitted through the first portion, the second spectrum of light transmitted through the second portion, or the third spectrum of light transmitted through the third portion. The optical system includes a single image sensor for receiving the at least two of the first, second, or third spectrums of light from the single lens and generating and transmitting data characterizing the at least two of the first, second, or third spectrums of light received from the single lens. The imaging system includes a memory element for storing computer executable instructions; and at least one processor configured to execute the computer executable instructions to generate, using the data, at least two of first, second, or third images of the first, second, or third portions, respectively.

According to aspects illustrated herein, there is provided an optical imaging system for use with an infusion tube having a drip chamber including a first portion with a drip tube, a second portion with an exit port, and a third portion located between the first and second portions, the optical imaging system including: a single light source for emitting at least two of first, second, or third spectrums of light; and an optics system including a single lens for receiving and transmitting at least two of: the first spectrum of light transmitted through the first portion; the second spectrum of light transmitted through the second portion; and the third spectrum of light transmitted through the third portion; and a single color image sensor for: receiving the at least two of the first, second, or third spectrums of light from the single lens; and generating and transmitting data characterizing the at least two of the first, second, or third spectrums of light received from the single lens. The imaging system includes a memory element for storing computer executable instructions, and at least one processor configured to execute the computer executable instructions to generate, using the data, at least two of first, second, or third images of the first, second, or third portions, respectively.

According to aspects illustrated herein, there is provided an optical imaging system for use with an infusion tube having a drip chamber including a first portion with a drip tube, a second portion with an exit port, and a third portion located between the first and second portions. The optical imaging system includes: at least one of a first light source for emitting a first spectrum of light only, a second light source for emitting a second spectrum of light only, or third source of light for emitting a third spectrum of light only; and an optics system including a single lens for receiving and transmitting at least one of: the first spectrum of light transmitted through the first portion; the second spectrum of light transmitted through the second portion; and the third spectrum of light transmitted through the third portion. The optical system includes a single color image sensor for receiving the at least one of the first, second, or third spectrums of light from the single lens and generating and transmitting data characterizing the at least one of the first, second, or third spectrums of light received from the single lens. The imaging system includes a memory element for storing computer executable instructions, and at least one processor configured to execute the computer executable instructions to generate, using the data, at least one of first, second, or third images of the first, second, or third portions, respectively. The first, second, and third spectrums of light are free of overlapping wavelengths amongst each other.

According to aspects illustrated herein, there is provided a method of imaging an infusion tube having a drip chamber including a first portion with a drip tube, a second portion with an exit port, and a third portion located between the first and second portions, including: storing, in a memory element, computer executable instructions; emitting at least two of first, second, or third spectrums of light from at least one light source; receiving and transmitting, using a single lens at least two of: the first spectrum of light transmitted through the first portion; the second spectrum of light transmitted through the second portion; or the third spectrum of light transmitted through the third portion; receiving, using a single image sensor, the at least two of the first, second, or third spectrums of light from the single lens; generating and transmitting, using the single image sensor data characterizing the at least two of the first, second, or third spectrums of light received from the single lens; and executing, using the at least one processor, the computer executable instructions to generate, using the data, at least two of first, second, or third images of the first, second, or third portions, respectively.

According to aspects illustrated herein, there is provided a method of imaging an infusion tube having a drip chamber including a first portion with a drip tube, a second portion with an exit port, and a third portion located between the first and second portions, including: storing computer executable instructions in a memory element; emitting, using a single light source, at least two of first, second, or third spectrums of light: receiving and transmitting, using a single lens at least two of: the first spectrum of light transmitted through the first portion; the second spectrum of light transmitted through the second portion; or the third spectrum of light transmitted through the third portion; receiving, using a single color image sensor, the at least two of the first, second, or third spectrums of light from the single lens; generating and transmitting, using a single color image sensor, data characterizing the at least two of the first, second, or third spectrums of light received from the single lens; and executing, using at least one processor, the computer executable instructions to generate, using the data, at least two of first, second, or third images of the first, second, or third portions, respectively.

According to aspects illustrated herein, there is provided a method of imaging an infusion tube having a drip chamber including a first portion with a drip tube, a second portion with an exit port, and a third portion located between the first and second portions, including: storing computer executable instructions in a memory element; and emitting at least one of a first spectrum of light only using a first light source, a second spectrum of light only using a second light source; or a third spectrum of light only using a third light source. The method includes: receiving and transmitting, using a single lens at least one of: the first spectrum of light transmitted through the first portion; the second spectrum of light transmitted through the second portion; or the third spectrum of light transmitted through the third portion; receiving, using a single color image sensor, the at least one of the first, second, or third spectrums of light from the single lens; generating and transmitting, using the single color image sensor, data characterizing the at least one of the first, second, or third spectrums of light received from the single lens; and executing, using at least one processor, the computer executable instructions to generate, using the data, at least one of first, second, or third images of the first, second, or third portions, respectively. The first, second, and third spectrums of light are free of overlapping wavelengths amongst each other.

BRIEF DESCRIPTION OF THE DRAWINGS

The nature and mode of operation of the present invention will now be more fully described in the following detailed description of the invention taken with the accompanying drawing figures, in which:

FIGS. 3A through 3F illustrate example embodiments of the illumination system shown in FIG. 2;

FIGS. 4A through 4C are schematic representation of embodiments for an optical system;

FIGS. 8A and 8B are schematic details for a pump implementing an operation for determining a gravity vector;

FIGS. 9A and 9B are schematic details of a pump using light injection;

FIGS. 10A and 10B are schematic details of a pump with a meniscus detection arrangement;

DETAILED DESCRIPTION

At the outset, it should be appreciated that like drawing numbers on different drawing views identify identical, or functionally similar, structural elements of the invention. While the present invention is described with respect to what is presently considered to be the preferred aspects, it is to be understood that the invention as claimed is not limited to the disclosed aspects.

Furthermore, it is understood that this invention is not limited to the particular methodology, materials and modifications described and as such may, of course, vary. It is also understood that the terminology used herein is for the purpose of describing particular aspects only, and is not intended to limit the scope of the present invention, which is limited only by the appended claims.

Unless defined otherwise, all technical and scientific terms used herein have the same meaning as commonly understood to one of ordinary skill in the art to which this invention belongs. Although any methods, devices or materials similar or equivalent to those described herein can be used in the practice or testing of the invention, the preferred methods, devices, and materials are now described.

Figure 1:
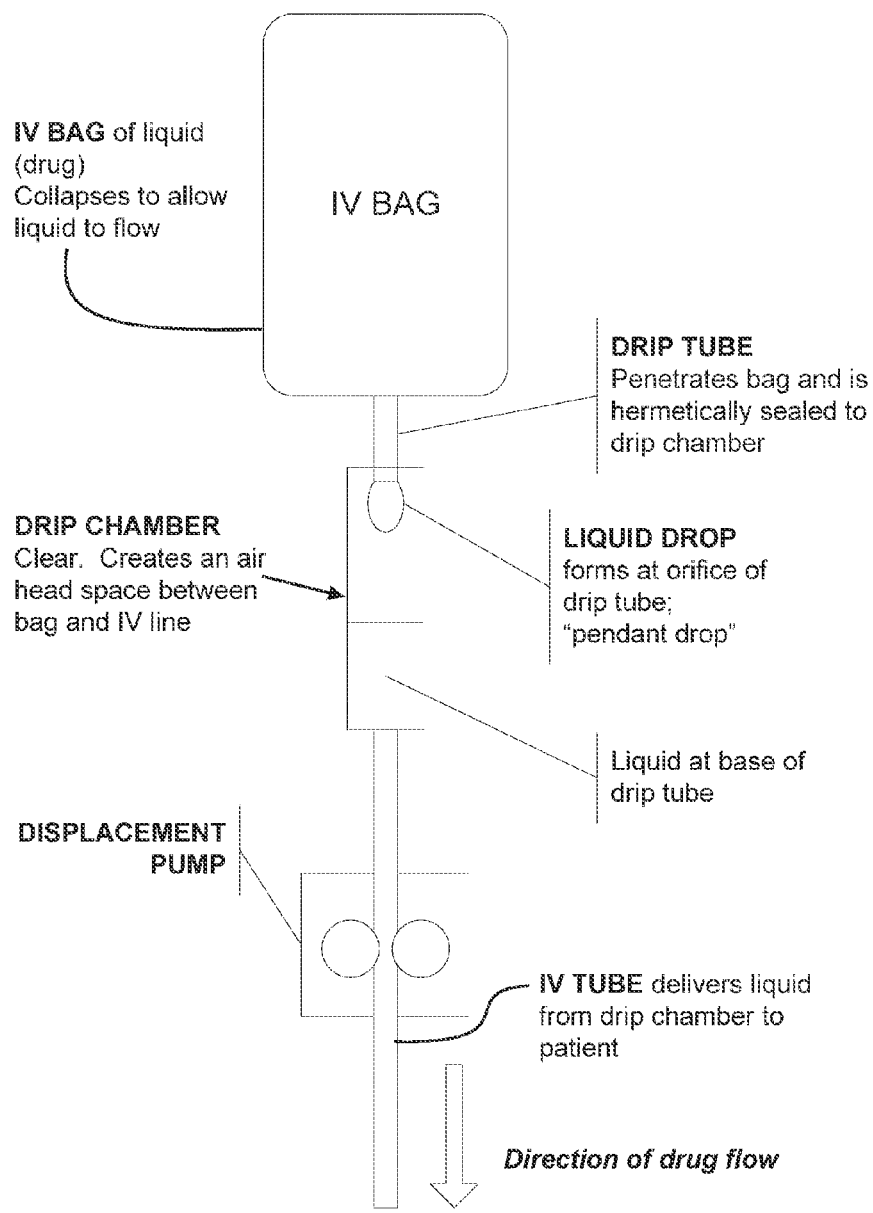
FIG. 1 is a schematic representation of definitions for an infusion pump.

FIG. 1 is a schematic representation of definitions for an infusion pump.

Figure 2:
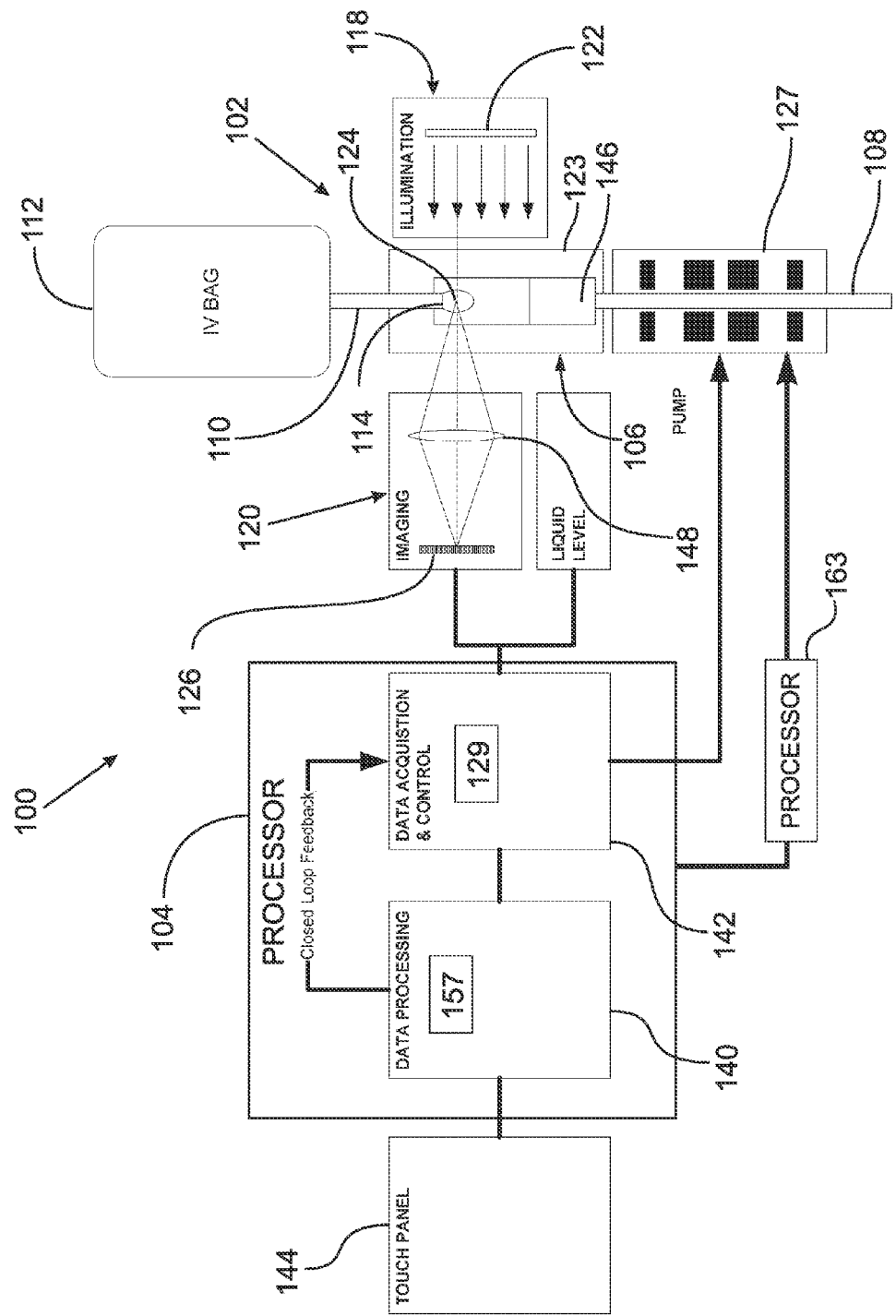
FIG. 2 is a schematic block representation of an infusion pump with an optical imaging system.

FIG. 2 is a schematic block representation of infusion pump 100 with optical imaging system 102. Pump 100 includes specially programmed microprocessor 104, drip chamber 106 for connection to output tube 108, and drip tube 110 for connecting the drip chamber to a source of fluid 112, for example, an IV bag. The drip tube includes end 114 disposed within the drip chamber. The imaging system includes illumination system 118 and optical system 120. System 118 includes lighting element 122 for transmitting light through wall 123 of the drip chamber to or around drop 124 of the fluid suspended from the end of the drip tube, for example, one or both of the drip and end 114 are illuminated. System 118 also controls illumination properties of the light transmitted to the drop. System 120 receives, for example using optical sensor 126, light transmitted through the drop, or through or around end 114 and transmits, to the microprocessor, data 129 regarding the received light. Pump 100 also includes pumping mechanism 127. In one embodiment, the mechanism includes top and bottom flow restrictors and uses peristaltic actuators, such as rollers, to displace fluid through tube 108.

Figure 3A:
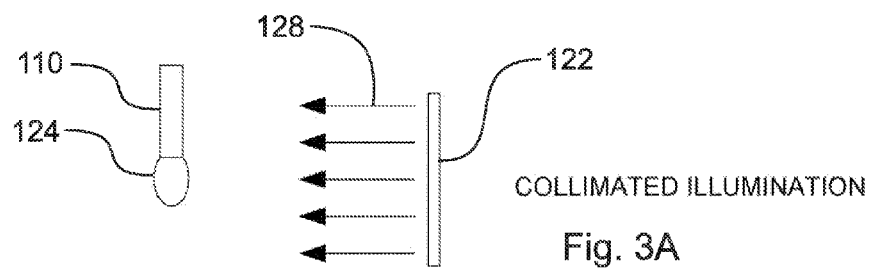
Figure 3B:
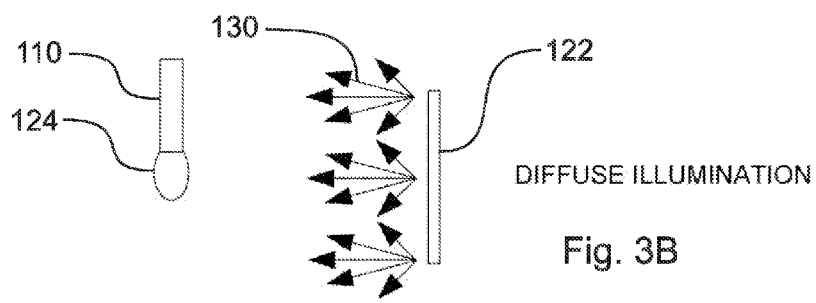
Figure 3C:
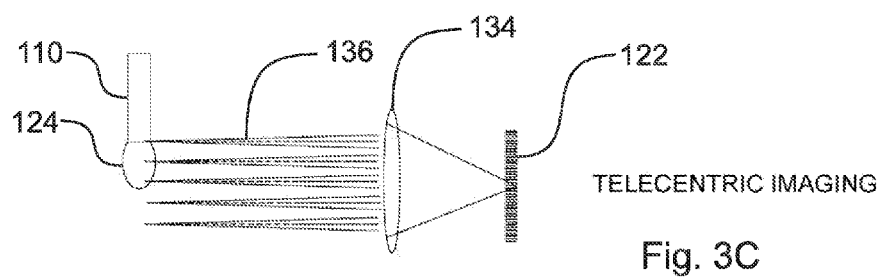
Figure 3D:
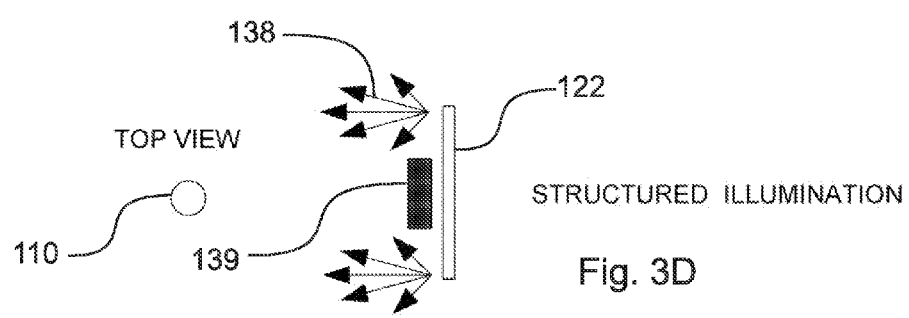

FIGS. 3A through 3F illustrate example embodiments of system 118 in FIG. 2. As shown in FIG. 3A, light rays 128 from a collimated illumination system are parallel. As shown in FIG. 3B, light rays 130 from a diffuse illumination system are emitted in a cone-shaped pattern from each light emitting point on an illumination plane. As shown in FIG. 3C, light rays 132 from illumination source 122 pass through telecentric lens 134 and are formed into ray bundles 136. The rays in bundles 136 are very nearly parallel. The ray bundles provide sharp definition of image edges and minimize depth distortion As shown in FIG. 3D, a structured lighting element shapes illumination, for example, rays 138, so as to control unwanted or stray light and to accentuate edges of an objecting being illuminated. A structured lighting element can include barrier 139, disposed between an illumination source and an object being illuminated, for example, drop 124, to shape the illumination, for example, by blocking or altering light emanating from the source.

FIG. 3E illustrates the use of laser interference to project stripe patterns measure drop 124. Illumination source 122 includes laser light sources 187. Sources 187 project light patterns consisting of many stripes at once, or of arbitrary fringes. This technique enables the acquisition of a multitude of samples regarding an image of drop 124, simultaneously. As seen from different viewpoints, the projected pattern appears geometrically distorted due to the surface shape of the object. In one embodiment, patterns of parallel stripes are used; however, it should be understood that other patterns can be used. The displacement of the stripes allows for an exact retrieval of the three dimensional (3D) coordinates of details on an object's surface, for example, the surface of drop 124. Laser interference works with two wide planar fronts 189 from laser beams 191. The interference of the fronts results in regular, equidistant line, or interference, patterns 193. Different pattern sizes can be obtained by changing the angle between the beams. The method allows for the exact and easy generation of very fine patterns with unlimited depth of field. FIG. 3E is a top view of pump 100 and sources 187 are shown disposed radially about axis 195 for drop tube 110. However, it should be understood that other configurations of sources 187 with respect to the pump are possible, for example, parallel to axis 195.

FIG. 3F illustrates the use of projection lens 196 in system 118. In FIG. 3F, system 118 illumination source transmits light 197 through lens 196. Surface 198 of the lens is modified as known in the art, for example, etched or through deposition of chrome or other materials, to produce a pattern on the surface. Light 197 passing through the lens projects an image of the pattern on and about drop 124. In one embodiment, projected pattern 199 is in the form of a constant-interval bar and space square wave, such as a Ronchi Ruling, or Ronchi grating.

The illumination source for a structured lighting element can be collimated, diffuse, or telecentric. Structured illumination can control unwanted or stray light and accentuate image edges. In one embodiment, the illumination system includes a telecentric lighting element. In one embodiment, the illumination system includes a structured lighting element.

Returning to FIG. 2, microprocessor 104 includes data processing segment 140 and data acquisition and control segment 142. The pump also includes control panel 144, for example, any graphical user interface known in the art. Output from the optical system, for example, data 129 from sensor 126, is inputted to segment 142. Panel 144, or other operator input, is used to input a desired flow rate through the drip chamber, as well as other necessary data such as drug type and treatment information. Microprocessor 104 can be any microprocessor known in the art.

Pump 100 uses optical sensing of pendant drops, that is drops hanging from or suspended from end 114, to measure fluid flow through the drip chamber to the output tube and to provide input to a closed-loop pump control process controlled by the microprocessor. Fluid from source 112 flows through drip tube to end 114 of the drip tube. The fluid forms drop 124 at end 114 and when conditions in the drip tube, discussed infra, are suitable, the drop falls from end 114 into fluid 146 in the drip chamber. In general, a pendant drop increases in volume in proportion to the outflow of fluid 146 from the drip chamber through tube 108. That is, an increase in the volume of the pendant drop during a time frame is equal to the volume of fluid passing from the drip chamber to tube 108 in the time period. The preceding relationship is based on the following assumptions: the fluid from the source is not compressible; source 112, the drip tube, the drip chamber, tube 108, and a patient to whom tube 108 is connected are closed to outside atmosphere. Each measurement of the drop volume is processed to provide a fluid volume (or mass) measurement. Successive measurements of drop volume over known intervals of time are used by the microprocessor to calculate the flow rate of fluid through the system.

Thus, in one embodiment, operation of pumping mechanism 127 is controlled by the microprocessor using the desired set point for flow through the drip chamber and data regarding a measured flow rate of fluid through the drip chamber. For example, the microprocessor executes a feedback loop which compares the desired flow rate with the measured flow rate, and adjusts the pumping mechanism to correct any deviations between desired and measured flow rates.

FIGS. 4A through 4C are schematic representation of embodiments for optical system 120. The embodiments shown in FIGS. 4A through 4C form real, conjugate images, for example, of drop 124 on a focal plane array formed by sensor 126. FIGS. 4A and 4B use refractive optics, such as single lens 148 or combinations 150 of lenses, respectively. FIG. 4C shows refractive optics, such as combination 150 of lenses, and reflective optics, such as fold mirror 152. Lens 148, combination 150, and mirror 152 can be any lens, combination of lenses, or mirror known in the art. Combination 150 may include different lenses in FIGS. 4B and 4C.

Returning to FIG. 2, in one embodiment, optical sensor 126 is a focal plane array formed by any means known in the art, including, but not limited to a charge coupled device (CCD), a CMOS detector, or a hybrid imaging array such as InGaAs bonded to a CMOS readout integrated circuit. System 120 includes optics, such as lens 148, focused on the location of drop 124. It should be understood that other optics can be used in system 120. In one embodiment, chamber 106 is substantially optically clear and system 118 directs light though the walls of the chamber to the optical system, for example, sensor 126. The light can provide back or side illumination of the drop. In one embodiment, system 102 is configured such that drop 124 and the focal plane array are optical conjugates and the focal plane array records an actual image of the drop. The imaging system captures drop images at a rate sufficient to observe the growth and detachment of a single drop.

In one embodiment, pump 100 satisfies two key metrics with respect to imaging drop 124. First, the frame rate (images per second) is sufficient to capture a sequence of images as the drop grows in size and detaches. Second, the exposure time (the amount of time the light is collected on the sensor for each specific image) is short enough to freeze the motion of the drop. Pump 100 generates images with clear edge definition, sufficient magnification (in terms of number of pixels across the drop), and a minimum number of artifacts such as glare.

In one embodiment, imaging system 102 and the microprocessor produce an accurate image of the drop that is then analyzed as described infra to determine the volume of the drop. Since the fluid drop has a uniform density, and any bubbles (occlusions) or entrainments are sufficiently small to be negligible, in one embodiment, only the outer surface of the drop is measured to calculate the volume of the drop. The preceding measurement is accomplished by imaging the drop with sufficient spatial resolution to accurately measure the boundary surface. A numeric integral over this boundary then provides the droplet volume.

Figure 5C:
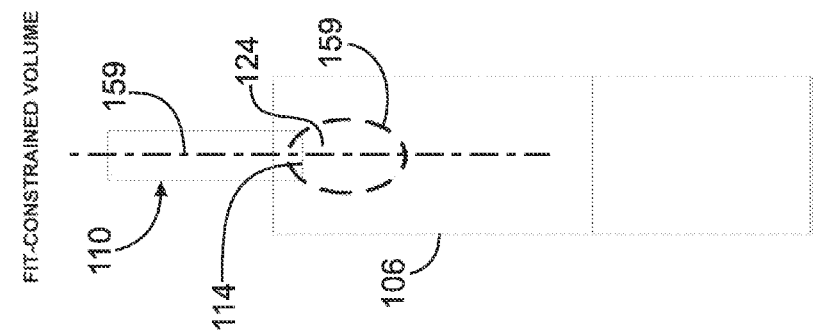
FIGS. 5A through 5C illustrate imaging processing definitions.
Figure 5B:
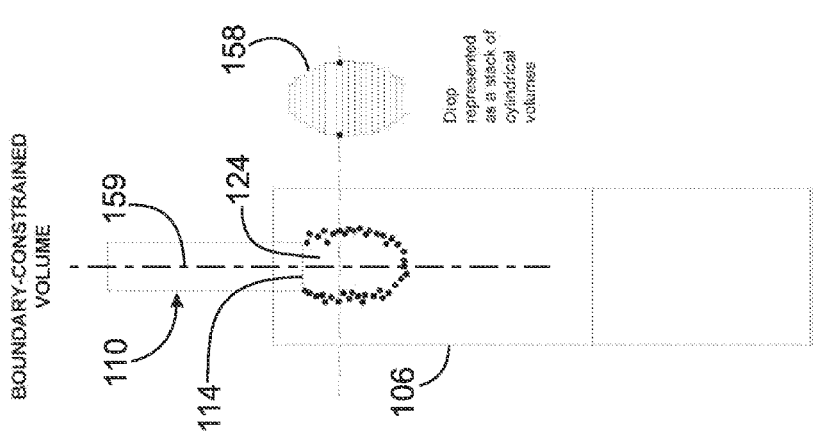
Figure 5A:
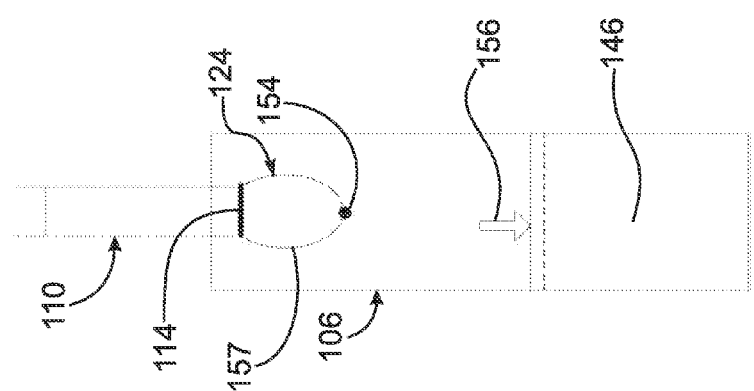

FIGS. 5A through 5C illustrate imaging processing definitions. In one embodiment, a reference/alignment frame and an image scale (pixels per mm) are established by locating end point 114 of the drip tube orifice, as shown in FIG. 5A. The end point has a known size and hence provides scale calibration. The end point also represents the top boundary of the drop, which is used in volume calculations described infra. In one embodiment, apex 154 of the drop (a point furthest from the fixed/reference point) is identified and used in the determination of the volume of the drop. For example, the optical system, for example, sensor 126, receives the light transmitted into or through the drip tube and transmitting, to the microprocessor, data regarding the received light. In one embodiment, the microprocessor is for determining, using the data, a boundary of end point 114 and using the boundary of end point 114 as a reference point for determining a volume, shape, or location of the drop, as further described infra.

In one embodiment, as further described infra, the direction of gravity (gravity vector 156) with respect to drop 124 is determined. A reference point, for example, the boundary of end point 114, and the gravity vector are used to establish a reference frame for the image processing.

In one embodiment, volume of drop 124 is calculated by using the microprocessor to receive data 129 and generate an image of the drop from the data. The microprocessor locates an outer edge of the drop in the image to define boundary 157 of the drop. The microprocessor integrates an area enclosed by the boundary and calculates a volume of revolution for the drop with respect to axis 159 for the drop that intersects the end of the drip tube, assuming symmetry of the drop with respect to the axis.

The above calculation of the volume of drip 124 can be calculated using at least two broad approaches. The first approach, termed Boundary Constrained Volume and shown in FIG. 5B, uses the outer location of the drop image to calculate the total volume. Each horizontal row 158 of pixel data from the image has associated with it an outer left and right boundary. The area between these boundaries is treated as the two dimensional projection of a circular disk volume (the symmetric volume of rotation of the area). The drop image is integrated from end point 114 to the apex by summing the volume of each row. Boundary Constrained Volume obtains maximum resolution for each row of data.

The second approach is termed Fit Constrained Volume and is shown in FIG. 5C. That is, the volume of drop 124 is determined by fitting a parametric function to the boundary image of the drop and integrating the parametric function, again, assuming rotational symmetry. There are a number of possible fitting algorithms, as discussed below, but the result of any fit is a set of parameters to the assumed function that represents entire boundary 157. Fit Constrained Volume smoothes out row detail.

In one embodiment, the microprocessor creates a plurality of temporally successive images of the drop from data 129 and calculates a respective volume for the drop in each successive image or calculates respective time periods between detachment of successive drops from the end of the drip tube. By temporally successive images, we mean a series of images taken over a time period in chronological order. The microprocessor calculates a rate of increase for the volume of the drop using the respective volumes or the respective time periods. As noted above, flow out of the drip tube is substantially equal to the increase in the volume of the drop; therefore, the time periods between drops detaching from the end of the drip tube can be correlated to the volume increases of the successive drops. For example, in one embodiment, the microprocessor calculates a respective volume for the drop in each successive image, for example, using operations described infra and supra; calculates changes in the respective volumes; and calculates a flow rate of fluid to the output tube based on the changes in the respective volumes. In one embodiment, the microprocessor controls mechanism 127 to match the calculated flow rate with a desired flow rate, for example, stored in the microprocessor.

In one embodiment, the microprocessor is for generating a free flow alarm or an out of bound condition alarm when the rate of increase for the volume of the drops exceeds a predetermined value, for example, stored in the microprocessor. In one embodiment, the microprocessor is for operating mechanism 127 to shut off flow to the output tube when the free flow alarm or the out of bound condition alarm is generated. In one embodiment the microprocessor generates a downstream occlusion alarm when the rate of increase of the volume of the drop is less than a predetermined value. In one embodiment, the microprocessor determines that a drop is absent from the end of the drip tube for a specified period of time and generates an empty bag alarm or an air-in-line alarm.

In one embodiment, the pump includes processor 163 used to operate mechanism 127 to shut off flow to the output tube when the free flow alarm or the out of bound condition alarm is generated. That is, as a safety and redundancy factor, a second microprocessor is used in the pump.

The drop is initially hanging from a fixed point in the drip chamber, for example, end 114. In one embodiment, the microprocessor is for identifying when the drop detaches from the fixed point in the drip chamber as a means of determining when the drop has reached maximum volume. The microprocessor makes the preceding identification by creating a plurality of temporally successive images of the drop and analyzing these images. By temporally successive images, we mean a series of images taken over a time period in chronological order.

In one embodiment, the microprocessor identifies, in each successive image, a respective point in the boundary, for example, apex 154, and determines a distance of each respective point from end 114. The microprocessor then identifies two successive images of the drop in which the distance, noted above, in the second image in the succession is less than the distance in the first image in the succession. This decrease of the distance indicates that the drop detached from the fixed point in the interval between the first and second images, which further indicates that the drop reached a maximum size in the first image. The microprocessor calculates the volume of the drop using the first image.

Figure 6:
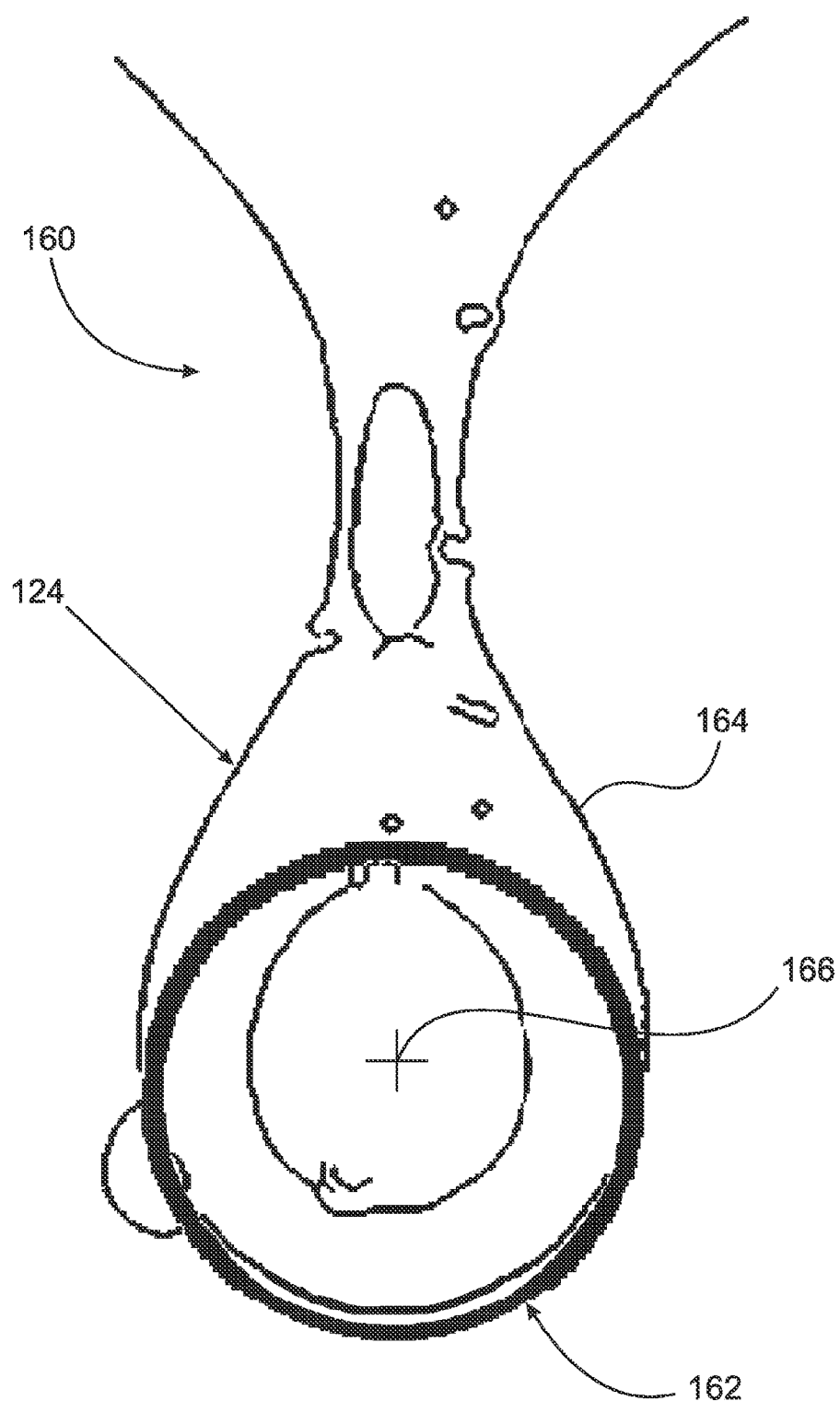
FIG. 6 illustrates an image of a drop including a circle at least partly included within an outer boundary of the drop

FIG. 6 illustrates image 160 of drop 124 including circle 162 at least partly included within outer boundary 164 of the drop. FIG. 6 illustrates a specific example of the Fit Constrained Volume approach. In one embodiment, the microprocessor identifies respective circles 162 within each temporally successive image. The circles are partially defined by a respective outer boundaries 164 of the temporally successive images. The microprocessor identifies a respective location, with respect to the fixed point in the drip chamber, for each respective circle and calculates a volume of the drop from the data and using the respective circles.

In one embodiment, identifying the respective location for said each respective circle includes identifying the image corresponding to the largest size of the drop, for example, the last image before the drop detaches from the end point of the drip tube. For example, the microprocessor identifies a respective point on each respective circle at a furthest distance from the fixed point in the drip chamber, for example, end point 114. The microprocessor then determines which of the respective points is furthest from the fixed point and identifies an image including the respective point furthest from the fixed point. That is, the microprocessor identifies the largest drop by identifying the drop having the largest circle. In one embodiment, the largest drop is identified by determining a first image in which the distance of the apex from the fixed point decreases with respect to the distance of the apex from the fixed point for a second image immediately preceding the first image. This decrease indicates that the drop detached from the fixed point in the interval between the first and second images, which further indicates that the drop reached a maximum size in the first image. The microprocessor calculates the volume of the drop using the image including the respective point furthest from the fixed point.

In one embodiment, the microprocessor identifies the respective outer boundaries for each of the temporal images such that each outer boundary includes a respective edge of the drop furthest from the fixed point in the drip chamber and the respective circle includes the respective edge. That is, the microprocessor aligns the circles described supra with the actual edges of the drops such that the points of the circles furthest from the fixed point, for example, end 114, are part of the edge of the drop. In one embodiment, the microprocessor identifies respective circular arcs corresponding to the respective edges and including the respective circular arcs in the respective circles.

In one embodiment, identifying the image corresponding to the largest size of the drop, for example, the last image before the drop detaches from the end point of the drip tube, includes using the center points of the circles. For example, the microprocessor calculates respective center points 166 for the circles and calculates the positions of the center points with respect to the fixed point, for example, end point 114. The microprocessor then determines which of the center points is furthest from the fixed point and identifies an image including the center point furthest from the fixed point. That is, the microprocessor identifies the largest drop by identifying the drop having the largest circle. The microprocessor calculates the volume of the drop using the image including the center point furthest from the fixed point.

Figure 7:
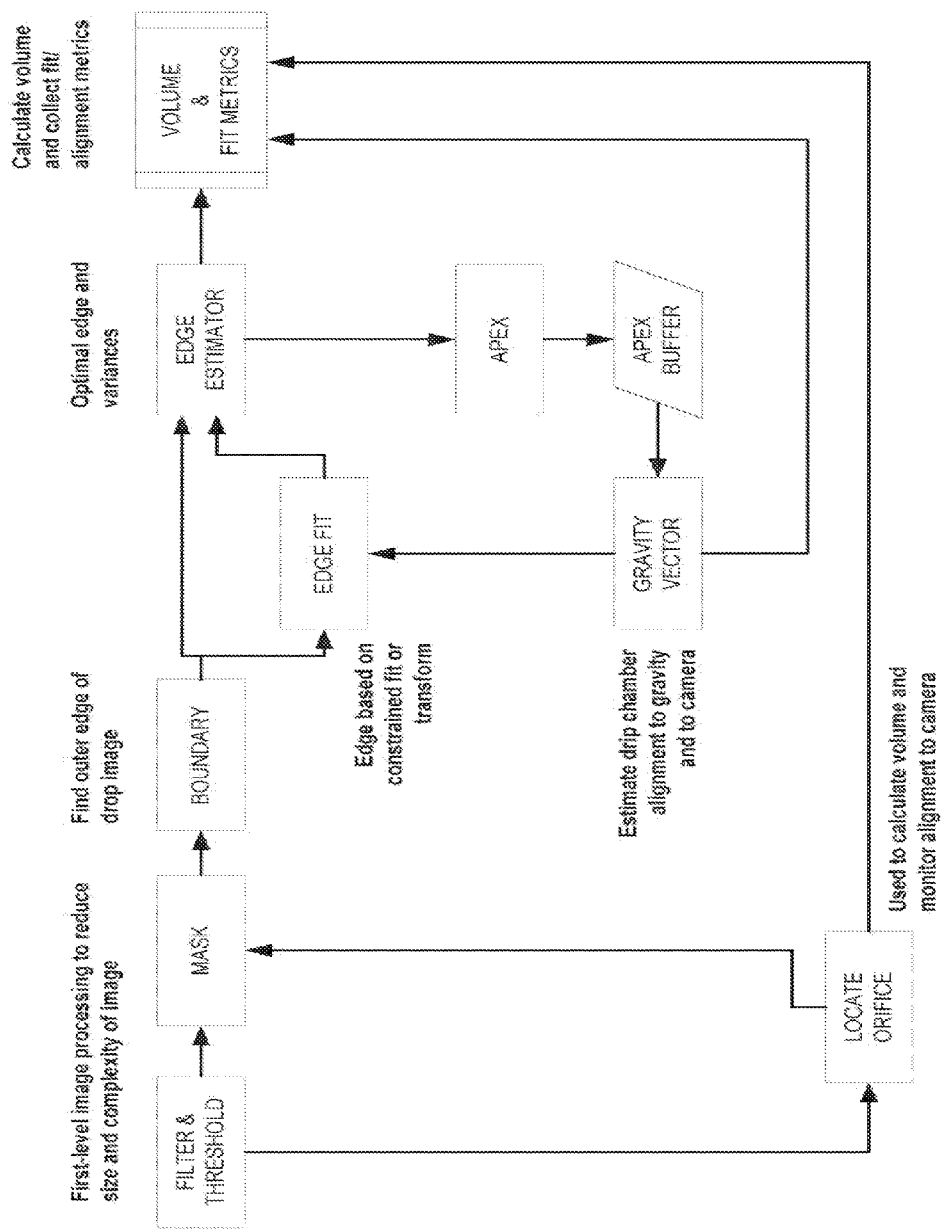
FIG. 7 is a flow chart illustrating operation of a pump with an optical imaging system.

FIG. 7 is a flow chart illustrating operation of pump 100 with an optical imaging system. FIG. 7 illustrates an example algorithm usable by pump 100. It should be understood that other algorithms are usable by the pump. The image of drop 124 is filtered and thresholded to create a binary image. Filter operations can include median filtering (to remove isolated glare), background and image uniformity correction (to remove noise sources due to dark noise, read noise, pixel non-uniformity, and illumination non-uniformity), and edge definition (using techniques such as convolution or unsharp masking). The resulting images are thresholded to yield binary images. A binary image consists of values that are either black or white, with no intermediate grayscale values. The images are also processed (in parallel with the above operations) to find the reference location, for example, end point 114, using techniques such as feature detection, pattern matching, or transform techniques such as the Radon transform. The end point location is used to form an image mask. A mask isolates a region of an image for further processing. Use of a mask increases computational speed, as well as eliminates artifact information from being further processed.

In one embodiment, the binarized, masked images are then processed row-by-row to find the extreme right- and left-boundaries. This boundary-constrained fit is one estimate of the drop edge shape. In one embodiment, the images are also processed using a fit-constrained algorithm. Such an algorithm applies constraints based on assumptions about the drop shape as discussed supra and infra. The constraints are used in a non-linear least squares optimization scheme to minimize the error between the parameterized constraint function(s) and the set of binarized edge images.

The two different edge approximations are provided to an Edge Estimator algorithm that compares fit-constrained images to boundary-constrained images. In the simplest instantiation, the images are compared row-by-row. The boundary-constrained images are considered to be the "correct" result unless they deviates from the fit-constrained images by more than a certain parameter (this parameter is adjusted during calibration). If the deviation is too large, the value from the fit-constrained image is used to replace that of the boundary-constrained image for that row. The above is intended to illustrate the concept behind the estimator. In actual use, more sophisticated algorithms are used to simultaneously optimize the difference between the two initial estimates. An example of such an algorithm is a Kalman filter, but other algorithms familiar to those skilled in the art may also be utilized.

The output from the Edge Estimator also provides the location of the apex of the drop, which is for example, used to calculate the time-dependent gravity vector. This operation requires access to prior estimates of the apex value (to calculate the change), and hence a number of prior values are stored in a buffer. The gravity vector is required for some of the parametric fit functions that are used in the fit-constrained edge estimation algorithms. Hence, the gravity vector is used in a feedback loop for the edge fit algorithms.

FIGS. 8A and 8B are schematic details for pump 100 implementing an operation for determining gravity vector 156. In one embodiment, system 118 illuminates end point 114 and drop 124 and the optical system, for example, sensor 126, receives light emanating from the end point and light emanating from the drop and transmits data 129 regarding the received light. The microprocessor generates, using the data, respective images of the drop and the end of the drip tube and locates an apex of the drop, the apex being a portion of the drop at a furthest distance from the end of the drip tube. The microprocessor determines, using the location of the apex, an orientation of the drop with respect to the end of the drip tube and calculates, using the orientation of the drop with respect to the end of the drip tube, an orientation of the drip chamber. In one embodiment, the microprocessor compares the orientation of the drip chamber to a set point, for example, a certain orientation with respect to plumb stored in the microprocessor, and generates an out of bound condition alarm when the orientation equals the set point or varies from the set point by a specified amount. For example, if the drip chamber is too far out of plumb, operation of pump 100 may be compromised and the alarm is generated.

For example, in FIG. 8A line 168 for the actual orientation of the drop and axis 170 for the drip chamber are co-linear, Since the drop must necessarily align with the forces of gravity (is plumb), the drip chamber is in a plumb orientation in FIG. 8A. Also, line 168 is aligned with gravity vector 156. In FIG. 8B, lines 168 and 170 are not co-linear and the drip chamber is not plumb. Thus, in one embodiment, the microprocessor generates lines 168 and 170 and compares the respective locations or orientation of the lines. That is, the microprocessor calculates the orientation of the drip chamber with respect to the gravity vector. In one embodiment, when data 129 is used to generate respective images over a period of time (temporally sequential images), the gravity vector is determined by measuring in the images of the end of the drip tube and the drop, the location of the apex of the pendant drop as it grows over time and tracking the time-dependent directional change of the apexes over a series of these measurements. In one embodiment, the boundary of end 114 is calculated as described supra and the boundary is used as reference plane for calculating the orientation of the drop and/or the drip chamber.

In one embodiment, the illumination system controls illumination properties of the light illuminating the end of the drip tube and the drop and the microprocessor: identifies respective boundaries of the end of the drip tube and the drop from the respective images; fits a parametric function to the respective boundaries; and integrating the parametric function to obtain a volume of the drop, for example, as described above.

In one embodiment, the end point location, gravity vector, and optimal edge estimate are input to a volume calculation routine that integrates the edge image using the "circular disk" assumption discussed above. The location of the end of the drip tube is used to determine the upper limit of integration, while the gravity vector is used to determine the direction of the horizontal (at right angles to the gravity vector). These end and gravity data values are provided along with the volume as output from the algorithm. In one embodiment, the algorithm also passes out the parameters of the edge fit, as well as statistical data such as fit variances. In one embodiment, the preceding information is used in the digital signal processing chain discussed below.

A number of methods can be used to fit a constraint to the measured image. In one embodiment, a "pendant drop" approach, involves solving the Laplace-Young equation (LYE) for surface tension. A drop hanging from a contact point (the end point) has a shape that is controlled by the balance of surface tension (related to viscosity) and gravity. The assumption is only strictly valid when the drop is in equilibrium; oscillations (due to vibration or pressure fluctuations) will distort the drop shape from the Laplace-Young prediction. However, small oscillations will not cause the fit to fail; in fact, the deviation from a fit is itself a good indicator of the presence of such oscillations.

In one embodiment, a Circular Hough Transform (CHT) is used on the image to identify the component of the image that represents the curved bottom of the drop. While not strictly a "fit", the CHT provides a parametric representation of the drop that is characterized by the value and origin of the radius of a circle. The CHT algorithm is representative of a constraint that is determined or applied in a mathematical transform space of the image. Other widely-used transforms, familiar to those skilled in the art, are the Fourier and wavelet transforms, as well as the Radon transform.

The parametric fitting procedures described above apply strong constraints on the possible location of the edge of the drop. Along with the assumption of continuity (a fluid edge cannot deviate from its neighbors over sufficiently short distances), and the requirement that the drop edge terminate at the drip tube orifice, the procedures are used to augment and correct the boundary-constrained image, as discussed above. Other fitting procedures work similarly to those discussed herein.

FIGS. 9A and 9B are schematic details of pump 100 using light injection. Drip tube 110, drip chamber 106, tube 108, drop 124, imaging system 120, and sensor 126 are as described for FIG. 2. Illumination system 118 includes illumination source 172 for transmitting, or injecting, light 174 into the drip tube. The light reflects off a plurality of portions of internally facing surface 176 of the drip tube and the reflected light is transmitted through the end point 114 of the drip tube into interior 177 of drop 124 such that the interior is uniformly illuminated. The optical system receives light 178 transmitted from the interior of the drop and transmits, to the computer processor, data regarding the received light. The data regarding the received light can be operated upon using any of the operations noted supra. For example, in one embodiment, the illumination system is for controlling illumination properties of the light transmitted to the drop, and the optical system is for receiving light from the drop. The microprocessor is for: generating an image from the data, the image including a boundary of the drop; fitting a parametric function to the boundary of the drop; and integrating the parametric function to obtain a volume of the drop.

Thus, light 174 is formed into a beam, which is injected into the transparent drip tube so as to undergo significant internal reflection (i.e., equal to or greater than the so-called "critical angle"). The cylindrical bore of the tube causes the internal reflections to diverge inside the tube (filling the bore of the tube), while imperfections in the tube surface introduce light scattering. The result is that the drop is illuminated internally. Under these conditions the imaging optics in system 120 receive only light that is scattered from the drop surface (there is no direct ray path for the light to reach the lens). In addition to a high contrast edge image, this approach enables the use of a very compact illumination element.

FIG. 10A is a schematic detail of pump 100 with a meniscus detection arrangement. Drip tube 110, drip chamber 106, tube 108, and fluid 146 are as described for FIG. 2. Imaging system 102 includes light source, for example, a laser, for transmitting light 182 at an acute angle with respect to longitudinal axis 184 for the drip chamber, into the drip chamber such that the light reflects, at the acute angle, off a surface 186 of fluid pooled within the drip chamber. System 102 also includes sensor, or position sensitive detector, 188 for receiving reflected light 182 and transmitting, to the computer processor, data regarding the received light. The microprocessor is for calculating a position of surface 186 using the data regarding the received light.

The location on sensor 188 receiving light 182 depends on the location of surface 186. Levels 190A and 190B show two possible levels for fluid 146 and hence, two possible locations for surface 186. As seen in FIG. 10B, light 182A and 182B reflecting from levels 190A and 190B, respectively, strike different portions of sensor 188. The microprocessor uses the difference between the locations on sensor 188 to determine the level of fluid 146, that is, the meniscus, in the drip chamber. Sensor 188 can be any positional sensitive detector known in the art, for example, a segmented sensor or a lateral sensor. In one embodiment, the microprocessor generates an empty bag alarm or an air-in-line alarm for an instance in which the light transmitted from light source 188 is not received by the optical system, for example, the drip chamber is empty or level 186 is so low that light 182 does not strike fluid 146.

A segmented positional sensitive detector includes multiple active areas, for example, four active areas, or quadrants, separated by a small gap or dead region. When a symmetrical light spot is equally incident on all the quadrant, the device generates four equal currents and the spot is said to be located on the device's electrical center. As the spot translates across the active area, the current output for each segment can be used to calculate the position of the spot. A lateral positional sensitive detector includes a single active element in which the photodiode surface resistance is used to determine position. Accurate position information is obtained independent of the light spot intensity profile, symmetry or size. The device response is uniform across the detector aperture, with no dead space.

FIG. 10B is a schematic detail of pump 100 with a meniscus detection arrangement. In one embodiment, imaging system 102 includes mirror 192 on the opposite side of the drip tube to reflect light 182 back through the drip tube and beam splitter 194 to direct the reflected light to sensor 188. This configuration enables placement of all the electronics for the optical components on the same side of the tube.

The following provides further detail regarding meniscus level measurement. The drip chamber remains partially filled with fluid at all times during operation. The air trapped in the drip chamber is in pressure equilibrium with the fluid above and below it. The difference in pressure across the air gap drives fluid out of the bottom of the drip chamber and through downstream tubing 108. Fluid enters and leaves the drip tube chamber continuously as the drop grows in volume, and hence the meniscus level of the fluid remains nearly constant. However, changes in the meniscus level can occur for several reasons: transient changes may occur when a drop detaches and falls into the fluid below; or fluctuations may occur due to pressure oscillations in the fluid (due to pump vibration, motion of the tubing set, or motion of the patient). These transient changes will fluctuate around a mean meniscus value, and hence do not indicate changes in flow rate over times long compared to the characteristic fluctuation times.

Variations that change the mean meniscus level over longer times may occur due to changes in the external pressure environment (e.g., in a traveling vehicle or aircraft), changes in backpressure arising from medical issues with the patient, or due to occlusions or other malfunctions in the pumping process. These long-term meniscus level changes represent a concomitant change in the overall flow rate, and may be used to provide a refinement to the flow measurements described supra. Hence, it may be desired to monitor the level of the meniscus during the infusion, and to use the information derived therein as an indicator of operational problems with the infusion system, or as an adjunct to the primary optical flow measurement.

The method described above for measuring the level of fluid 146 uses the reflection of a light beam from the top surface of the fluid in the drip chamber. The axis of the reflected beam is shifted (deflected) laterally as the fluid level changes, for example, as shown by light 182A and 182B. The amount of deflection depends only on the fluid level change, and on the incident angle of the beam. Although a laser light source is shown in the figure, the technique is compatible with any light beam. Further, although the beam is shown freely propagating, the system may also incorporate lens elements to control the beam.

In one embodiment (not shown), sensor 126 (the imaging focal plane array) is used both for imaging drop 124 and measuring the meniscus of fluid 146 via beam splitters and other simple optics. Sensor 126 can be shared in at least two ways: a portion of the sensor that is not used for pendant drop imaging can simultaneously record the deflected beam; or illumination system 118 for pendant drop imaging and meniscus level measurement can be alternated in time, such that the sensor alternately records the drop image and the deflected beam image. For example, pump 100 can combine the imaging systems 102 shown in FIGS. 2 and 10A/10B or shown in FIGS. 2 and 9A.

Thus, in one embodiment, system 102 includes a first light source, such as light source 172 for transmitting light into the drip tube such that the light reflects off an internally facing surface of the drip tube, and the reflected light is transmitted through the end of the drip tube into an interior of a drop of the IV fluid hanging from the first end of the drip tube. System 102 also includes a second light source, such as light source 188, transmitting light, at an acute angle with respect to a longitudinal axis for the drip chamber, into the drip chamber such that the light reflects, at the acute angle, off a surface for IV fluid disposed within the drip chamber. Optical sensor 126 is for: receiving the reflected light transmitted from the interior of the drop; receiving the reflected light from the second light source; and transmitting, to the computer processor, data regarding the received light from the first and second light sources. The microprocessor is for calculating a volume of the drop using the data regarding the light received from the first light source, and calculating a position of the surface of the using the data regarding the light received from the second light source, as described supra.

Figure 11:
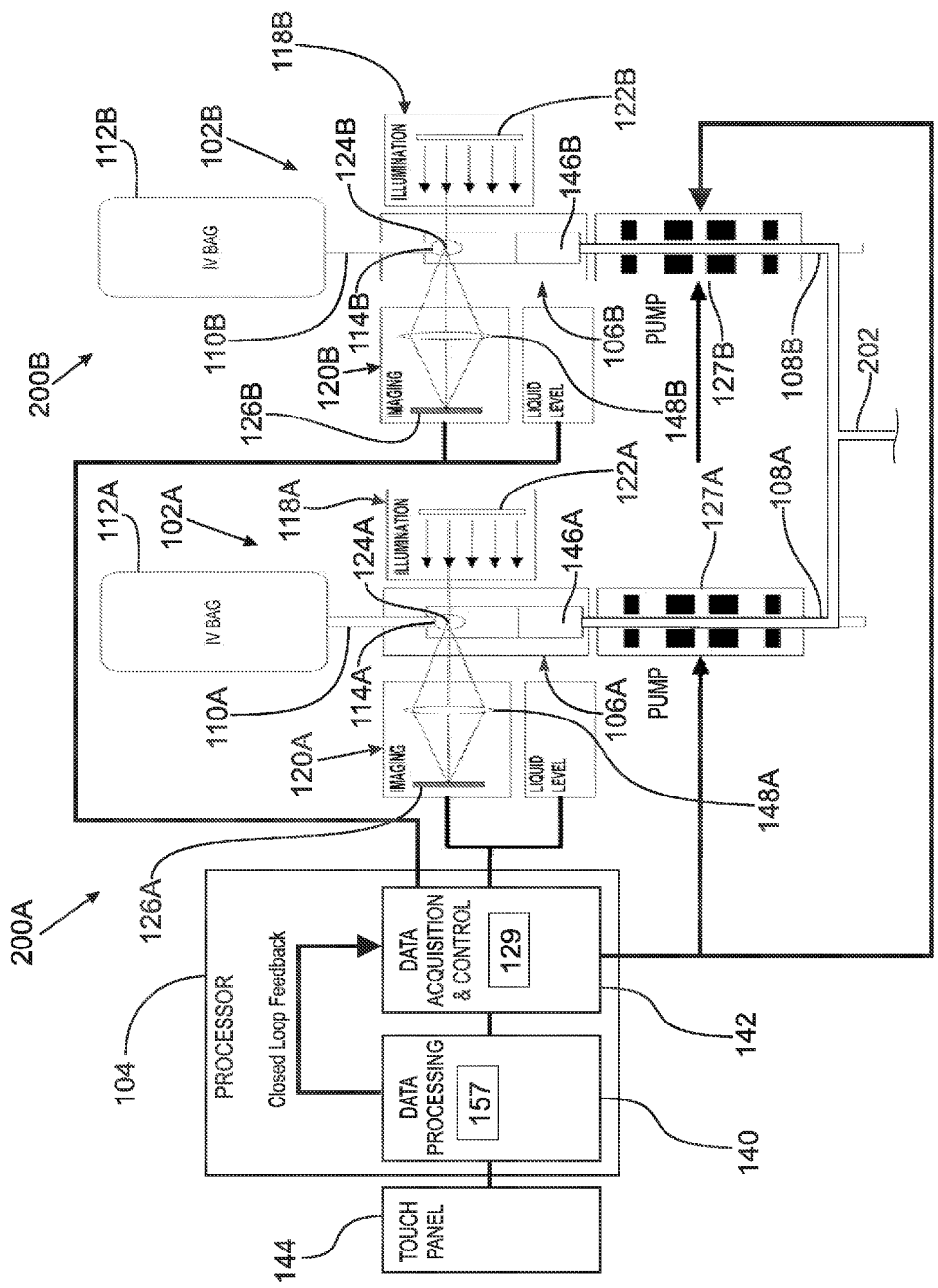
FIG. 11 is a schematic block representation of two infusion pumps with respective optical imaging system in a primary and secondary configuration.

FIG. 11 is a schematic block representation of pump assemblies 200A and 200B with respective optical imaging system in a primary and secondary configuration. The assemblies include the components for pump 100 described supra, with the exception of the processor and control panel. In general, the description above regarding the operation of pump 100 is applicable to the operation of assemblies 200A and 200B. Assembly 200A is connected to primary fluid source 112A. Pump 200B is connected to primary fluid source 112B. Sources 112A and 112B are arranged in a primary/secondary infusion configuration. For example, a primary medication in source 112A is administrated in coordination with a secondary medication in source 112B. As is known in the art, in a primary/secondary configuration, the medication in the secondary source is infused before the medication in the primary source. Tubings 108A and 108B from pump mechanisms 127A and 127B, respectively, are connected to common tubing 202.

In one embodiment, a single processor and control panel, for example, processor 104 and panel 144 are used for assemblies 200A and 200B. The processor operates assembly 200B according to appropriate protocols until the regime for the fluid in source 112B is completed. Then, the processor automatically deactivates assembly 200B as required and begins the infusion of the fluid in source 112A. In one embodiment (not shown), each assembly has a separate processor and control panel or each assembly has a separate processor and a common control panel.

Figure 12:
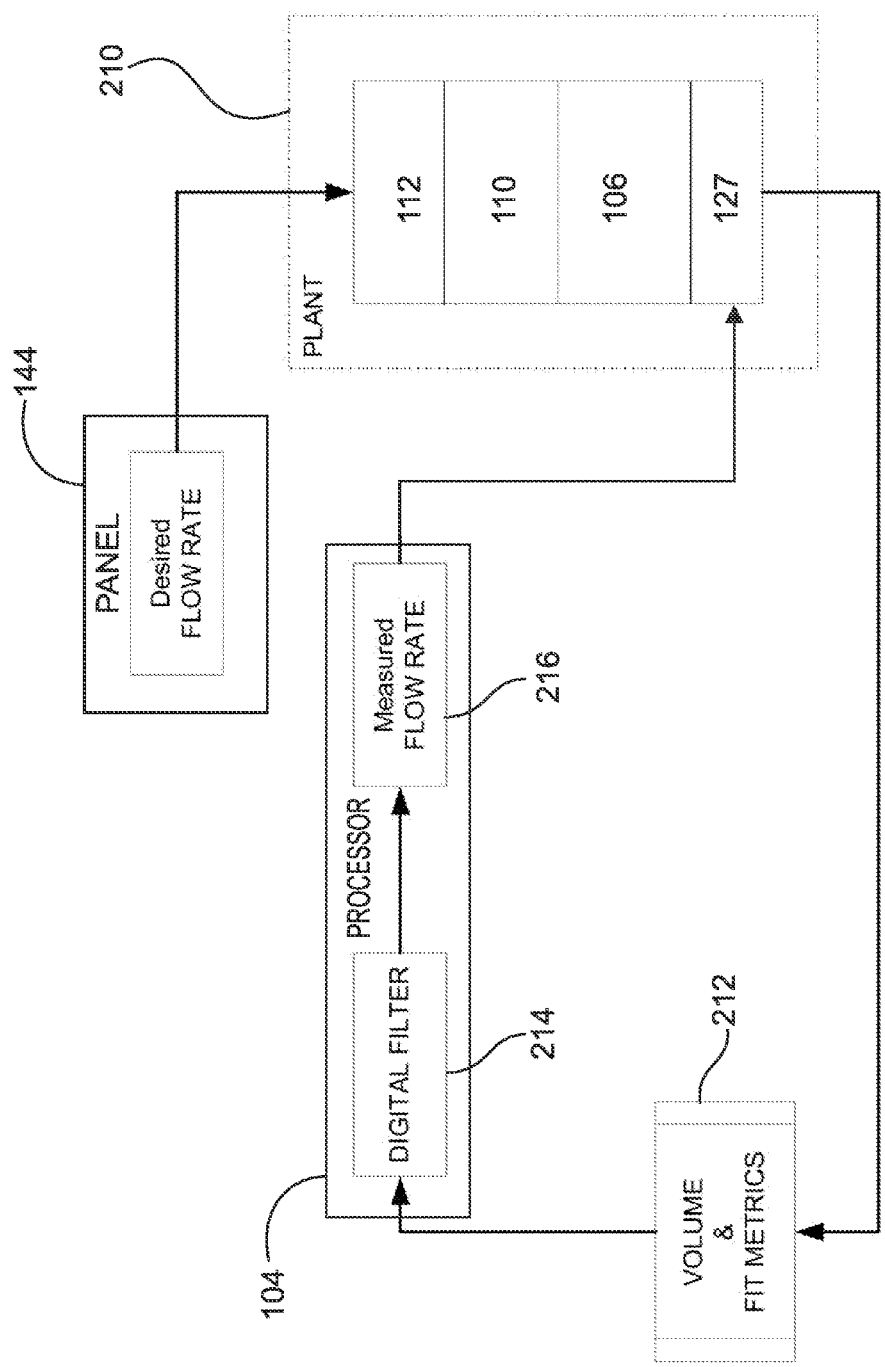
FIG. 12 is a top-level block diagram illustrating operation of a pump with an optical imaging system.

FIG. 12 is a top-level block diagram illustrating operation of pump 100 with an optical imaging system. In one embodiment, the volume measurement, and fit metrics if applicable, described above are fed into a digital signal processing algorithm that calculates the flow rate and provides feedback to the pump control system. Plant 210 includes source 112, the drip chamber, the drip tube, and pump mechanism 127. The microprocessor outputs the Volume and Fit Metrics 212, which are filtered by digital filter 214 in a portion of the microprocessor to provide measured flow rate 216. The measured flow rate is compared with the desired flow rate, for example, input into the microprocessor via panel 144, closing the feedback loop for pump 100.

Figure 13:
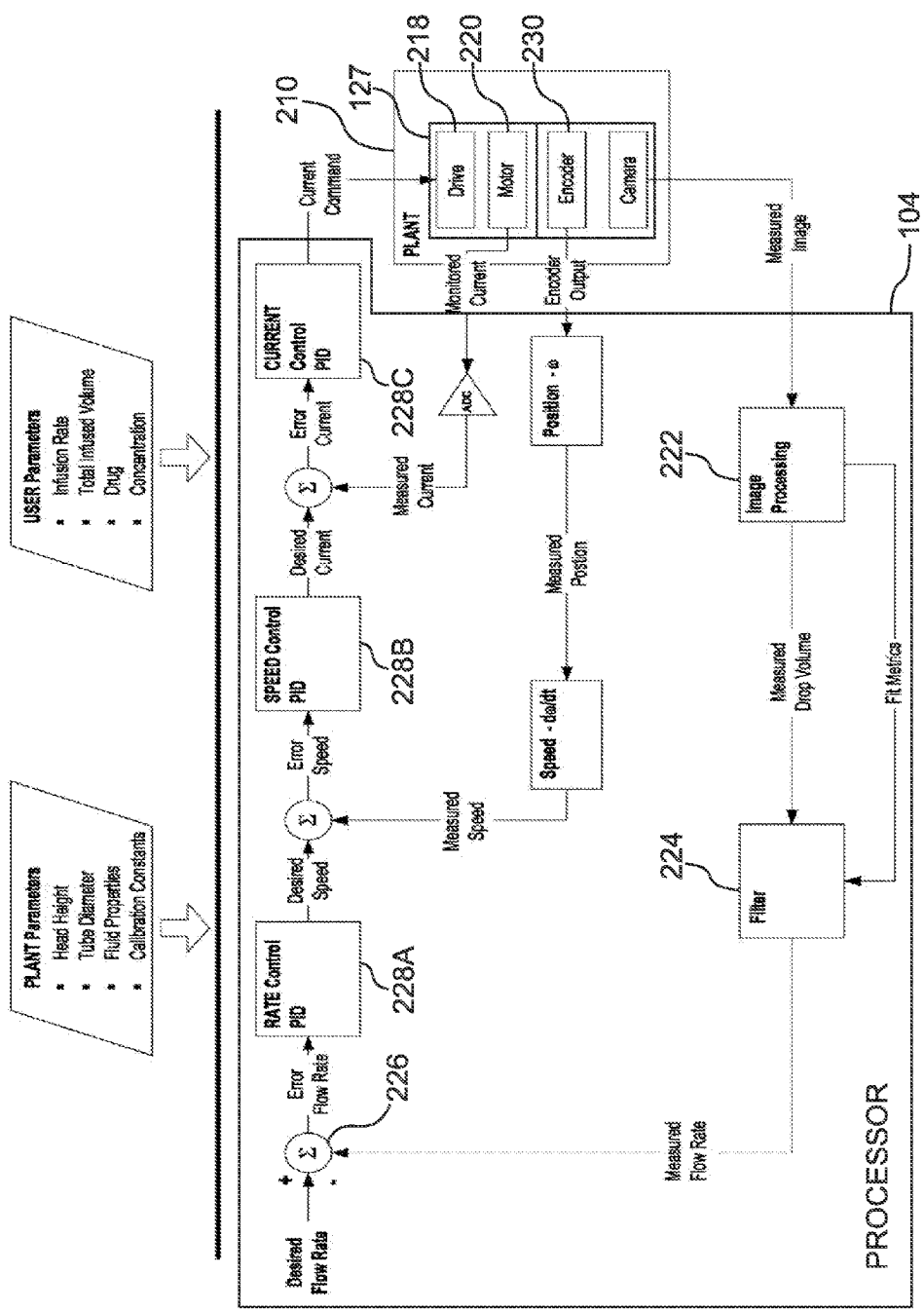
FIG. 13 is a block diagram illustrating example signal processing and feedback control for a pump with an optical imaging system.

FIG. 13 is a block diagram illustrating example signal processing and feedback control for pump 100 with an optical imaging system. Mechanism 127 includes drive 218 and motor 220. Imaging data from system 102 is processed by image processing block 222 to generate a Measured Drop Volume, and the results are input to filter block 224. The output of the filter block is the Measured Flow Rate. The Measured Flow Rate is compared to the Desired Flow Rate by comparator 226, providing the Error Flow Rate (error estimate). The Error Flow Rate feeds into a staged series of PID (Proportional, Integral, Derivative) control algorithms 228. Each PID block operates on a successively faster time scale. Block 228A controls the flow rate, block 228B controls the pump motor speed, and block 228C controls the pump motor current. The speed control incorporates feedback from motor position encoder 230. The current control incorporates feedback from a motor current sensor in motor 220.

Figure 14:
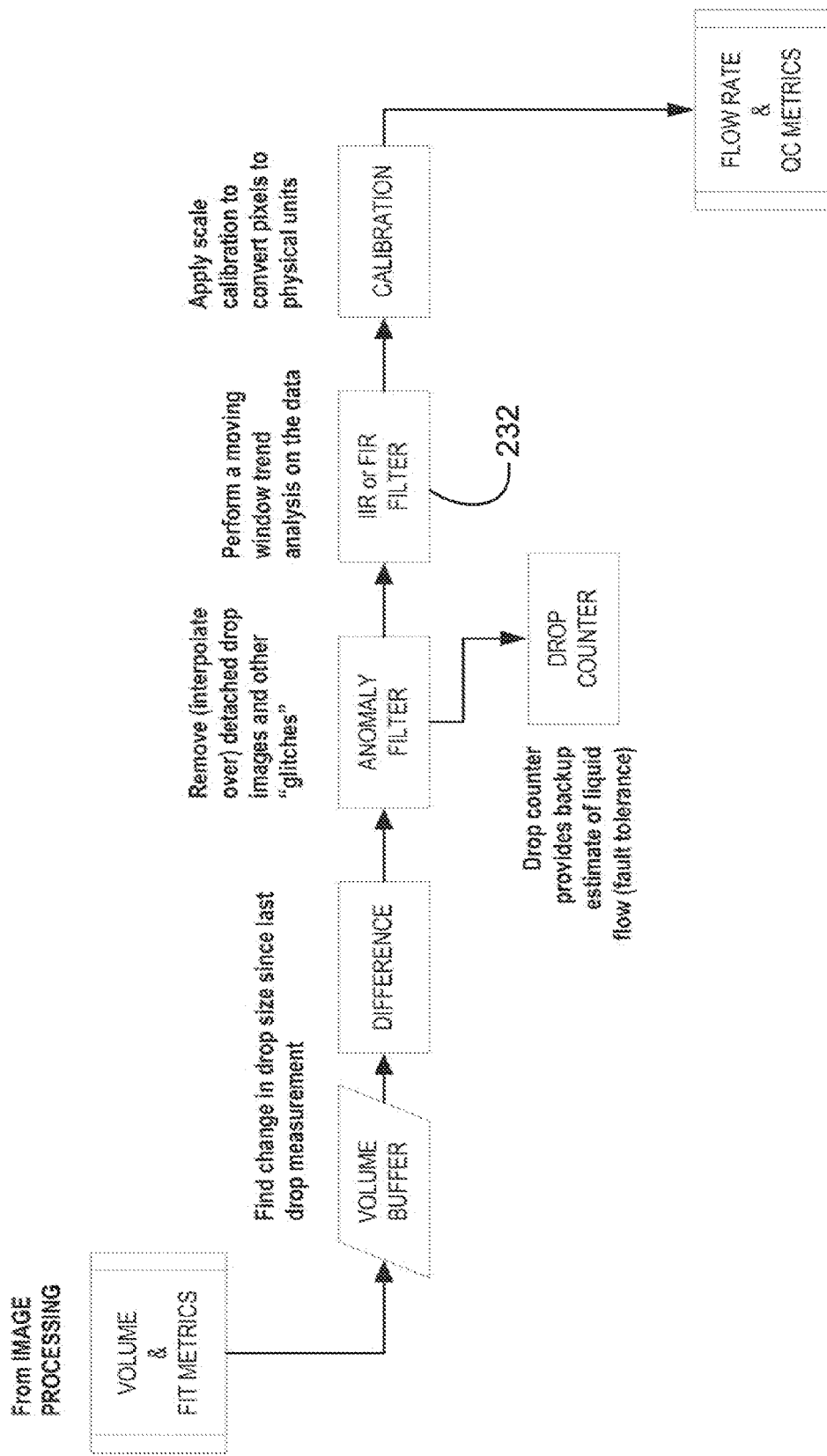
FIG. 14 is a block diagram illustrating example digital filtering in a pump with an optical imaging system.

FIG. 14 is a block diagram illustrating example digital filtering in pump 100 with an optical imaging system. Filter 232 can be any filter known in the art, for example, the general class of FIR/IIR filters known to those skilled in the art. A simple example is an FIR filter that implements a time average over a number of samples.

Figure 15:
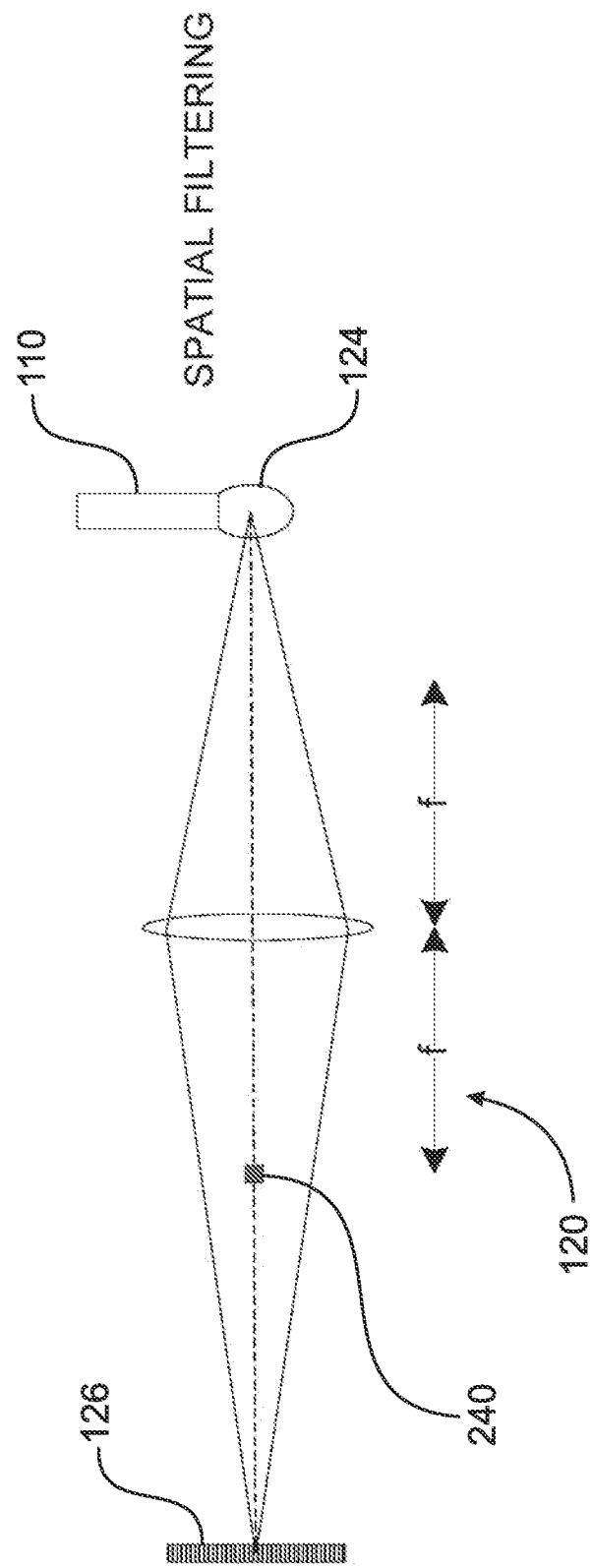
FIG. 15 is a schematic representation of example spatial filtering in a pump with an optical imaging system.

FIG. 15 is a schematic representation of example spatial filtering in pump 100 with an optical imaging system. The goal of high resolution and edge definition for images of drop 124 are attained by illumination techniques, optical techniques, or both, for example, as described supra. In one embodiment, spatial filtering techniques are used in the optics for system 120. For example, mask 240 at the back focal plane of imaging system 102 modifies (via optical Fourier transform) the image generated by the optical system, for example, sensor 126. A DC block filter is shown in FIG. 15. This filter blocks the central cone of the transmitted light and enhances edge images (associated with scattered light).

In one embodiment, the sensitivity of sensor 126 is matched to the illumination spectrum of the light source in system 118. In one embodiment, sensor 126 is a low-cost visible light sensor (400-1000 nm wavelength) and source 122 generates light that is outside the range of human visual perception (i.e., 800-1000 nm). In this case the operator will not be distracted by the bright illumination source.

It should be understood that pump 100 can be any pump mechanism or pump application known in the art and is not limited to only IV infusion pump applications. In the case of a gravity-fed system, the pumping mechanism can be replaced by a valve or flow restrictor, and still be compatible with the configurations and operations described supra.

Figure 16:
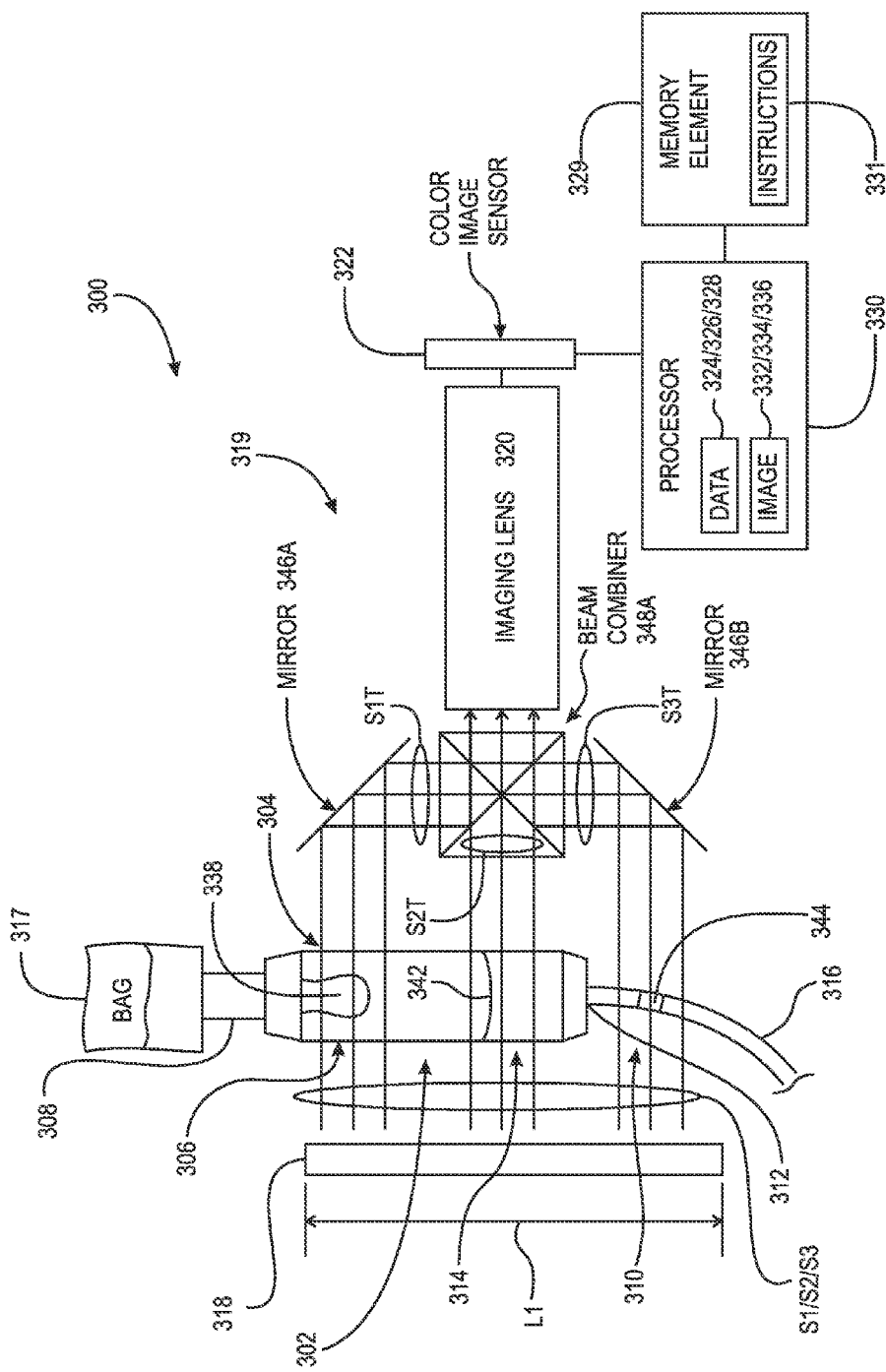
FIG. 16 is a schematic representation of an optical imaging system with multiple imaging channel optical sensing and a single light source.

FIG. 16 is a schematic representation of optical imaging system 300 with multiple imaging channel optical sensing. In an example embodiment, system 300 is used with infusion tube 302 including drip chamber 304. Drip chamber 304 includes portion 306 with drip tube 308, portion 310 including exit port 312, and portion 314 between portions 306 and 310. Output tube 316 can be connected to exit port 312 for flowing fluid out of drip chamber 304. Drip tube 308 is for connection to source of fluid 317, for example, medication bag 317. System 300 includes at least one light source 318 for emitting spectrums S1, S2, and S3 of light, and optical system 319.

Light source 318 can be any light source known in the art, including, but not limited to a light-emitting diode (LED), an array of LEDs, a laser diode, an incandescent lamp, or a fluorescent lamp.

The optical system includes single lens 320 for receiving and transmitting S1T, S2T, and S3T. S1T, S2T, and S3T include spectrums S1, S2, and S3, transmitted through portions 306, 310, and 314, respectively. Optics system 319 includes single image sensor 322 for receiving S1T, S2T, and S3T from single lens 320. Sensor 322 generates and transmits data 324, 326, and 328, characterizing S1T, S2T, and S3T, respectively, received by lens 320. System 300 includes memory element 329 and at least one specially programmed processor 330. Memory element 329 is configured to store computer executable instructions 331. Processor 330 is configured to execute instructions 331 to generate, using data 324, 326, and 328, images 332, 334, and 336 of portions 306, 310, and 314, respectively.

By "characterize" we mean that the respective data describes, or quantifies, the spectrum of light, for example, providing parameters enabling generation of an image using the respective data. By "emitting light" we mean that the element in questions generates the light. By "transmitted by" we mean passing light through the element in question, for example, light emitted by light source 318 passes through portions 306, 310, and 314.

In an example embodiment, sensor 322 is a color image sensor. In an example embodiment, light source 318 is a single light source.

In an example embodiment, portion 306 includes drop 338 pendant from drip tube 308 and image 332 includes an image of drop 338. Processor 330 is configured to execute instructions 331 to determine a volume of pendant drop 338 using image 332. The volume can be used in control schemes to regulate flow of fluid through infusion tube 302.

In an example embodiment, portion 314 includes meniscus 342 for fluid in drip chamber 304 and image 336 includes an image of meniscus 342. Processor 330 is configured to execute instructions 331 to determine a position of meniscus 342 using image 336. The position can be used in control and alarm schemes to regulate flow of fluid through infusion tube 302. In an example embodiment, air bubble 344 is present in portion 310 and processor 330 is configured to execute instructions 331 to determine a volume of air bubble 344 using image 334. The volume can be used in alarm schemes to ensure safe operation of infusion tube 302.

In an example embodiment, light source 318 emits red, blue, and green spectrum light. In an example embodiment, S1T consists of one of the red, blue, or green spectrum light, S2T consists of one of the red, blue, or green spectrum light not included in S1T, and S3T consists of one of the red, blue, or green spectrums of light not included in S1T or S2T. Thus each of S1T, S2T, and S3T consists of one of red, blue, or green light not included in the other of S1T, S2T, and S3T. That is, each of S1T, S2T, and S3T is different from the others. By "red spectrum light" we mean light including wavelengths between about 610 nm and 675 nm, with peak intensity at about 625 nm. By "blue spectrum light" we mean light including wavelengths between about 410 nm and 480 nm, with peak intensity at about 470 nm. By "green spectrum light" we mean light including wavelengths between about 500 nm and 575 nm, with peak intensity at about 525 nm. Thus, the respective spectrums for red, blue, and green light do not have overlapping wavelengths.

In an example embodiment, system 300 includes mirror 346 for reflecting one only of S1T, S2T, and S3T. For example, mirror 346A reflects S1T. In an example embodiment, system 300 includes mirror 346A for reflecting one only of S1T, S2T, or S3T, and mirror 346B for reflecting another only of S1T, S2T, or S3T, for example, S3T. In an example embodiment, system 300 includes beam combiner 348A for reflecting two only of S1T, S2T, or S3T. For example, in FIG. 16, beam combiner 348A reflects S1T and S3T and transmits S2T.

The following provides further detail regarding FIG. 16. As described below, various filtering operations are used to generate S1T, S2T, and S3T. Mirror 346A receives the combined red, blue, and green spectrums emitted by source 318 and transmitted by portion 306 of drip chamber 304, but reflects only spectrum S1T. Mirror 346B receives the combined red, blue, and green spectrums emitted by source 318 and transmitted by portion 310 of output tube 316, but reflects only spectrum S3T. Thus, mirrors 346A and 346B are color-filtering.

In an example embodiment, sensor 322 is not monochrome, that is, sensor 322 is a color image sensor. Beam combiner 348A transmits only spectrum S2T emitted by source 318 and transmitted by portion 314 of drip chamber 304. Specifically, beam combiner 348A receives the combined red, blue, and green spectrums emitted by source 318 and transmitted by portion 314 of drip chamber 304, but only transmits spectrum S2T. The beam combiner also reflects spectrum SiT reflected by mirror 346A and spectrum S3T reflected by mirror 346B. Note that the reflecting operations of beam combiner 348A can be implemented using broad-band reflection, since mirrors 346A and 346B have filtered out spectrums S2T and S3T and spectrums S1T and S2T, respectively.

Figure 17:
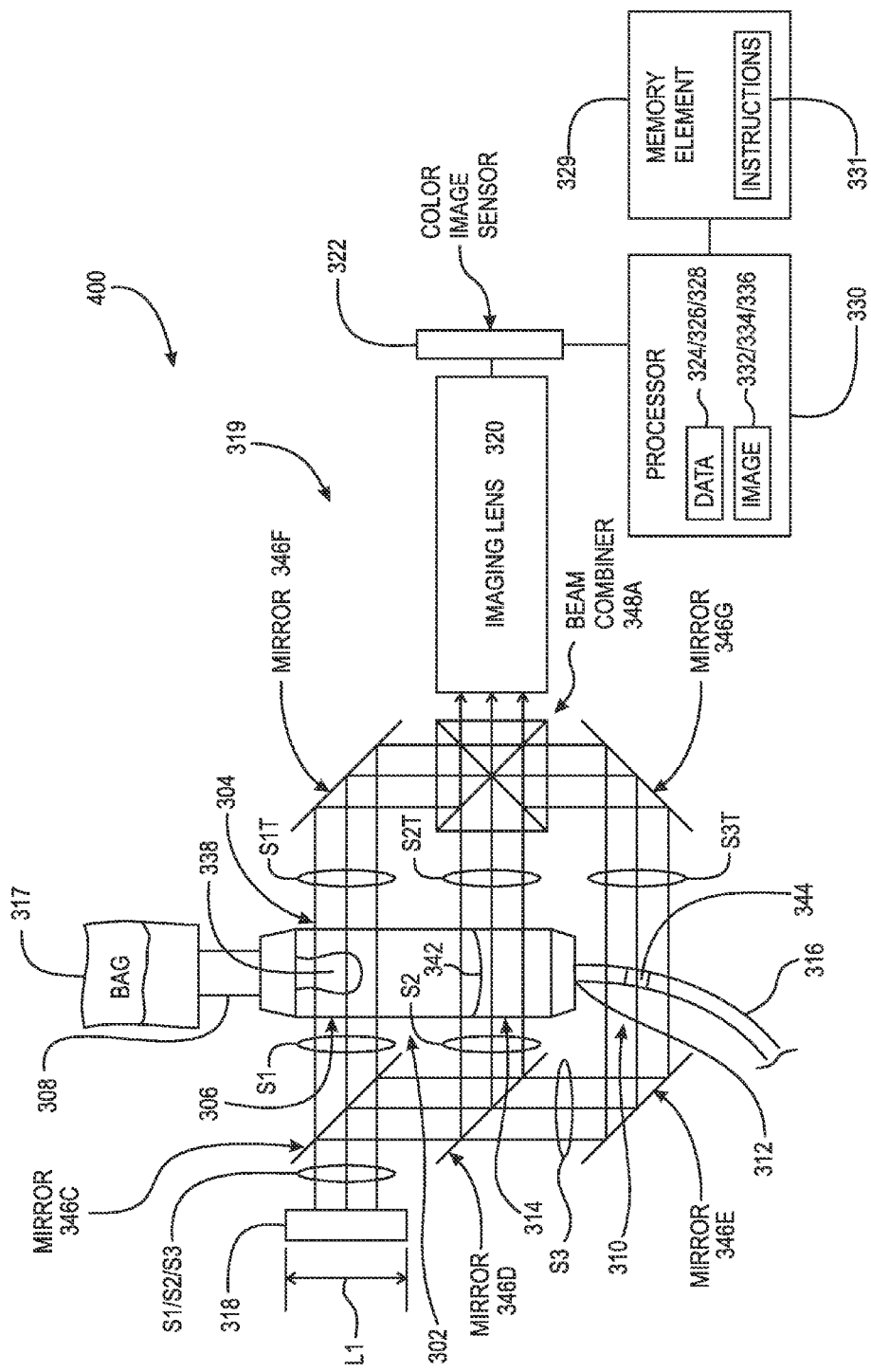
FIG. 17 is a schematic representation of an optical imaging system with multiple imaging channel optical sensing and a single light source.

FIG. 17 is a schematic representation of optical imaging system 400 with multiple imaging channel optical sensing. The discussion regarding system 300 is applicable to pump 400 except as follows. In an example embodiment: optics system 319 includes a mirror for transmitting to one of portions 306, 310, or 314 one only of S1, S2, or S3; or optics system 319 includes a mirror for reflecting to one of portions 306, 310, or 314, one only of S1, S2, or S3. For example: mirror 346C transmits S1 to portion 306 and reflects S2 and S3; mirror 346D transmits S3 and reflects S2 to portion 314; and mirror 346E reflects S3 to portion 310. In an example embodiment, mirror 346E is a broad-band reflecting mirror.

Mirror 346F is for reflecting spectrum S1T transmitted by portion 306 of drip chamber 304 to beam combiner 348A. In an example embodiment, mirror 346F is a broad-band reflecting mirror. Mirror 346G is for reflecting spectrum S3T transmitted by portion 310 of drip chamber 304 to beam combiner 348A. In an example embodiment, mirror 346G is a broad-band reflecting mirror. Since the light entering beam combiner 348A has been separated into discrete spectrums, for example, light from mirror 346G is only spectrum S2T, broad-band transmitting and reflecting operations can be used in beam combiner 348A.

Figure 18:
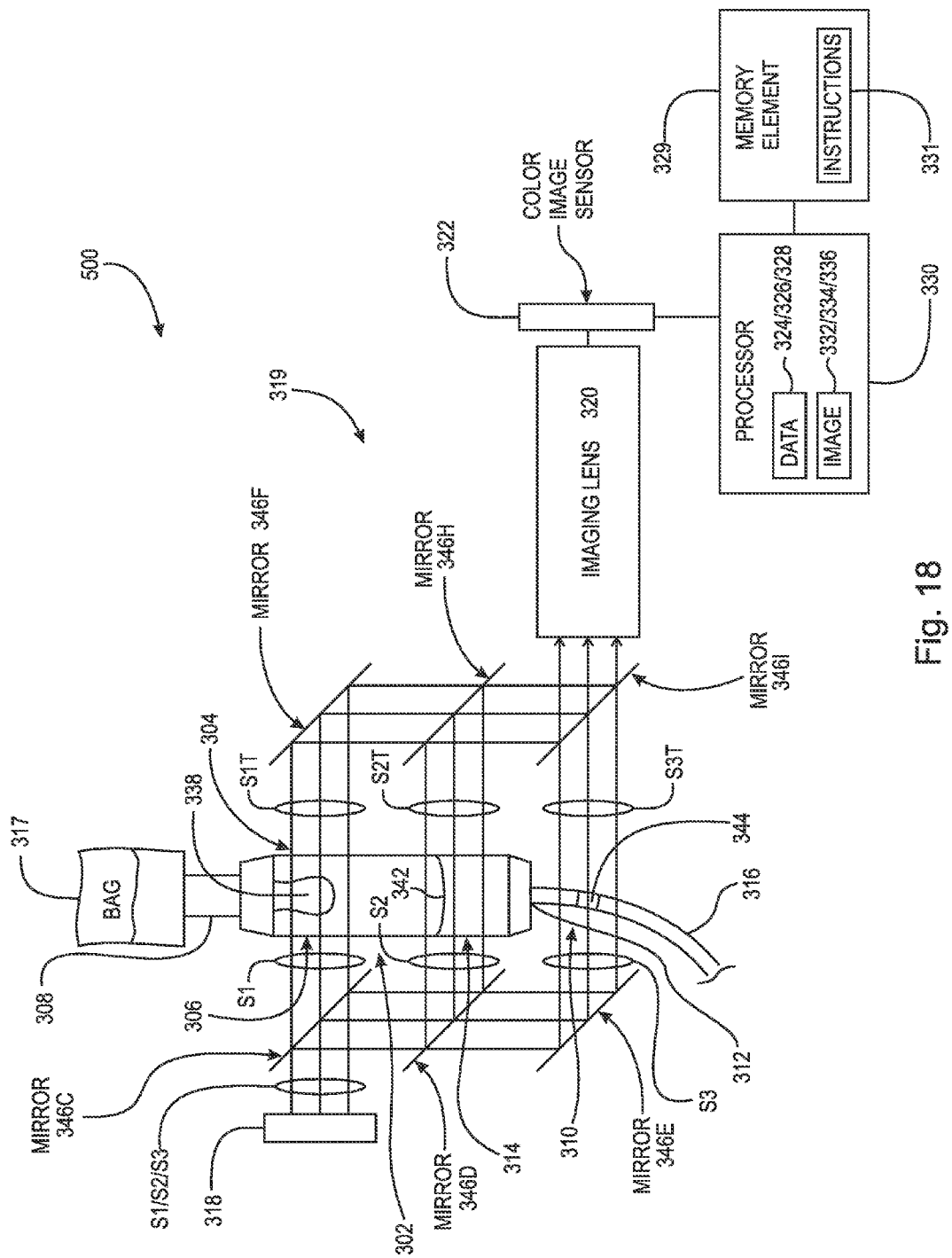
FIG. 18 is a schematic representation of an optical imaging system with multiple imaging channel optical sensing and a single light source.

FIG. 18 is a schematic representation of optical imaging system 500 with multiple imaging channel optical sensing. The respective discussions regarding systems 300 and 400 are applicable to system 500 except as follows. In an example embodiment, optical system 319 replaces a beam combiner with mirrors 346H and 346I. Mirror 346H transmits S1T reflected by mirror 346F and reflects S2T (from mirror 346D). Mirror 346I transmits S3T (from mirror 346E) and reflects S1T (transmitted by mirror 346H) and S2T (reflected by mirror 346H).

In FIG. 16, length L1 of light source 318 must be sufficient to span portions 306, 310, and 314, since light source 318 must emit light directly through portions 306, 310, and 314. However, in FIGS. 17 and 18 length L1 of light source 318 is considerably less, for example, equal only to length L2 of portion 306. In FIGS. 17 and 18, light source 318 is emitting light directly through portion 306; however, combinations of mirrors are used to reflect light to portions 310 and 314. Thus, a smaller and less expensive device can be used for light source 318 in FIGS. 17 and 18.

Figure 19:
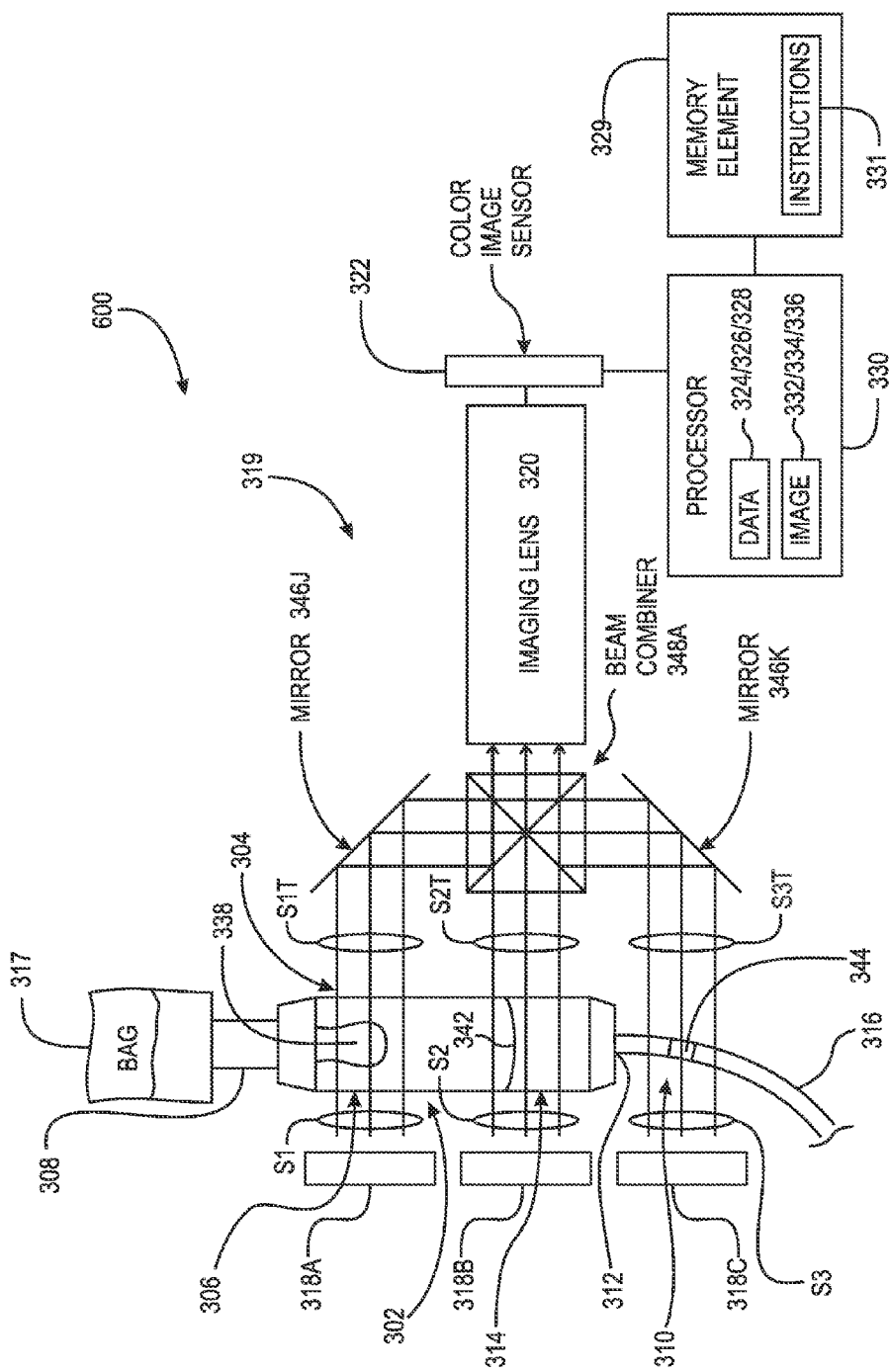
FIG. 19 is a schematic representation of an optical imaging system with multiple imaging channel optical sensing and multiple light sources; and, FIG. 20 is a schematic representation of an optical imaging system with two-channel optical imaging and a single light source.

FIG. 19 is a schematic representation of optical imaging system 600 with multiple imaging channel optical sensing. The discussion regarding system 300 is applicable to system 600 except as follows. System 600 includes three light sources: light source 318A for emitting only spectrum S1, light source 318B for emitting only spectrum S2, and light source 318C for emitting only spectrum S3. Optical system 319 includes mirror 346J for reflecting S1T and mirror 346K for reflecting S3T. Beam combiner 348B transmits S2T and reflects S1T and S3T. In an example embodiment, one or both of mirrors 346J and 346K are broad-band reflecting mirrors. In an example embodiment, beam combiner 348B has broad-band transmitting and reflecting functionality.

In respective example embodiments for system 300, 400, 500, and 600, two-channel imaging is performed for only two of portions 306, 310, or 314 and imaging is not performed on the remaining portion 306, 310, or 314.

Figure 20:
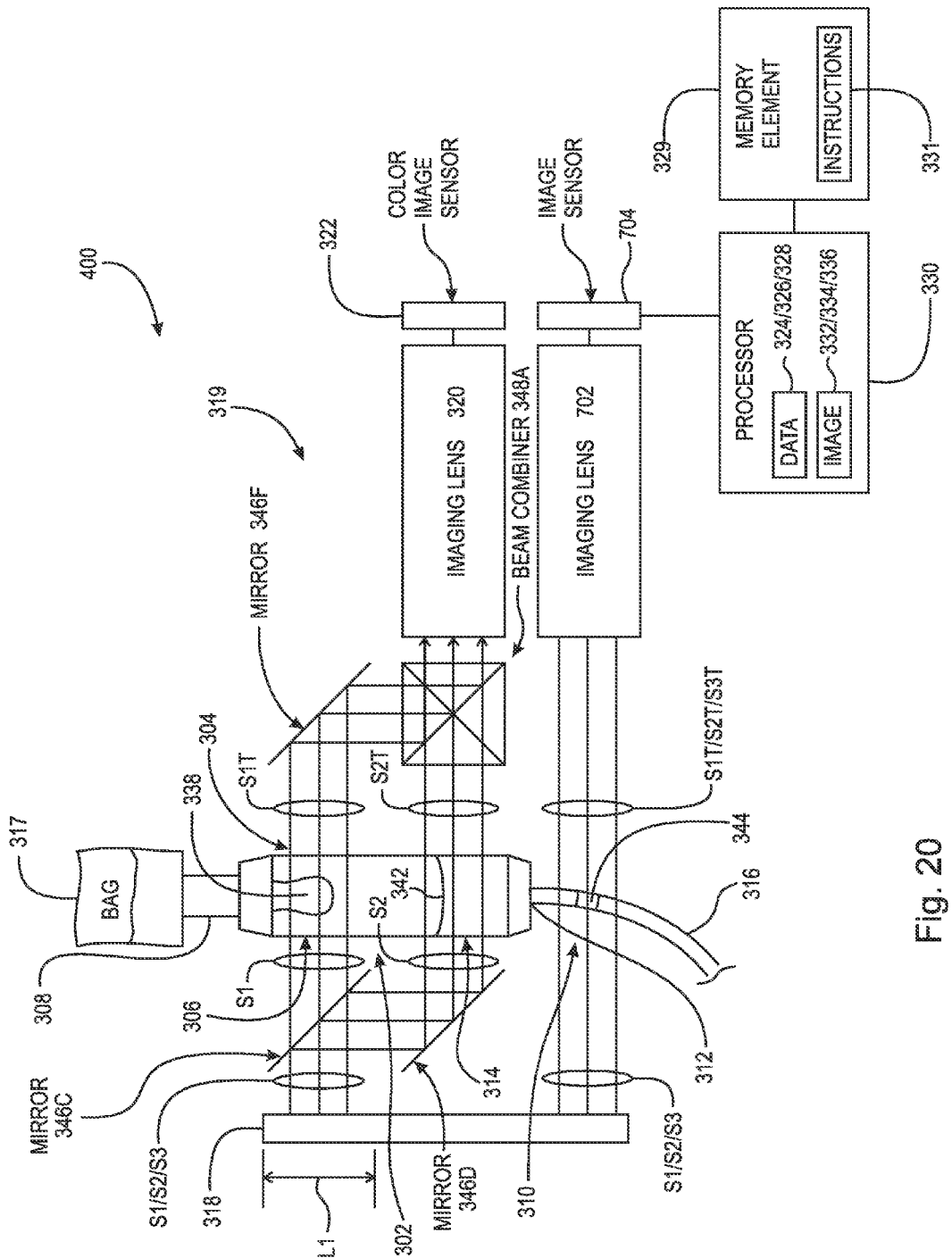

FIG. 20 is a schematic representation of optical imaging system 700 with two-channel optical imaging and a single light source. In system 700, chromatic multiplexing is implemented for only two of portions 306, 310, or 314. System 700 can use system 400 as a starting point. The following describes differences between systems 400 and 700 as shown. In FIG. 20, two-channel optical imaging is implemented for portions 306 and 314. Mirrors 346E and 346G are removed. Mirror 346D no longer is required to transmit S3. Beam combiner 348A is no longer required to reflect S3T. Otherwise, the operations regarding portions 306 and 314 are the same as described for FIG. 17. In an example embodiment, imaging of portion 310 is implemented by adding lens 702 to receive light S1T/S2T/S3T transmitted through portion 310 from light source 318. Lens 702 transmits S1T/S2T/S3T to image sensor 704, which generates data 326. Processor 330 generates image 334 from data 326. Image sensor 704 can be monochromatic, since chromatic multiplexing is not being implemented for portion 310.

Other combinations of two-channel optical sensing are possible for system 700 as is apparent to one skilled in the art. For example, mirror 346D can be removed such that two-channel optical sensing is performed for portions 306 and 310 only. Operations as described for portions 306 and 310 for FIG. 17 are substantially the same. Lens 702 receives S1T/S2T/S3T transmitted by portion 314 and transmits S1T/S2T/S3T to image sensor 704, which generates data 328. Processor 330 generates image 336 from data 328. Image sensor 704 can be monochromatic. For example, mirror 346F can be removed such that two-channel optical sensing is performed for portions 310 and 314 only. Operations as described for portions 310 and 314 for FIG. 17 are substantially the same. Lens 702 receives S1T/S2T/S3T transmitted by portion 306 and transmits S1T/S2T/S3T to image sensor 704, which generates data 324. Processor 330 generates image 332 from data 324. Image sensor 704 can be monochromatic. It should be understood that other configurations of components in system 400 are possible to implement two-channel optical imaging. In an example embodiment, two-channel imaging is performed for only two of portions 306, 310, or 314 and imaging is not performed on the remaining portion 306, 310, or 314. That is, a second lens and image sensor are not employed to image the remaining portion 306, 310, or 314.

System 300 can be modified for two-channel operation as is apparent to one skilled in the art. For example, two-channel operation can be implemented for portions 306 and 314 only by removing mirror 346B. Operations as described for portions 306 and 314 for FIG. 16 are substantially the same. S1T/S2T/S3T from portion 310 is received by a second lens (not shown) and transmitted to a second image sensor (not shown) that can be monochromatic. The second sensor generates data 326 for generating image 334. For example, two-channel operation can be implemented for portions 310 and 314 only by removing mirror 346A. Operations as described for portions 310 and 314 for FIG. 16 are substantially the same. S1T/S2T/S3T from portion 306 is received by a second lens (not shown) and transmitted to a second image sensor (not shown) that can be monochromatic. The second sensor generates data 324 for generating image 332. For example, two-channel operation can be implemented for portions 306 and 310 only. Operations as described for portions 306 and 310 for FIG. 16 are substantially the same. S1T/S2T/S3T from portion 314 is received by a second lens (not shown) and transmitted to a second image sensor (not shown) that can be monochromatic. The second sensor generates data 328 for generating image 336. It should be understood that other configurations of components in system 300 are possible to implement two-channel optical imaging. In an example embodiment, two-channel imaging is performed for only two of portions 306, 310, or 314 and imaging is not performed on the remaining portion 306, 310, or 314. That is, a second lens and image sensor are not employed to image the remaining portion 306, 310, or 314.

System 500 can be modified for two-channel operation as is apparent to one skilled in the art. For example, to implement two-channel operation for portions 306 and 314 only, mirror 346E can removed. Operations as described for portions 306 and 314 for FIG. 18 are substantially the same. S1T/S2T/S3T from portion 310 is received by a second lens (not shown) and transmitted a second image sensor (not shown) that can be monochromatic. The second sensor generates data 326 for generating image 334. For example, to implement two-channel operation for portions 310 and 314 only, mirror 346F can removed. Operations as described for portions 310 and 314 for FIG. 18 are substantially the same. S1T/S2T/S3T from portion 306 is received by a second lens (not shown) and transmitted a second image sensor (not shown) that can be monochromatic. The second sensor generates data 324 for generating image 332. For example, to implement two-channel operation for portions 306 and 310 only, mirrors 346D and 346H can removed. Operations as described for portions 306 and 310 for FIG. 18 are substantially the same. S1T/S2T/S3T from portion 314 is received by a second lens (not shown) and transmitted a second image sensor (not shown) that can be monochromatic. The second sensor generates data 328 for generating image 336. It should be understood that other configurations of components in system 500 are possible to implement two-channel optical imaging. In an example embodiment, two-channel imaging is performed for only two of portions 306, 310, or 314 and imaging is not performed on the remaining portion 306, 310, or 314. That is, a second lens and image sensor are not employed to image the remaining portion 306, 310, or 314.

System 600 can be modified for two-channel operation as is apparent to one skilled in the art. For example, to implement two-channel operation for portions 306 and 314 only, mirror 346K can removed. Operations as described for portions 306 and 314 for FIG. 19 are substantially the same. S3T from portion 310 is received by a second lens (not shown) and transmitted a second image sensor (not shown) that can be monochromatic. Light source 318C can be broadband (emit S1/S2/S3). The second sensor generates data 326 for generating image 334. For example, to implement two-channel operation for portions 310 and 314 only, mirror 346J can removed. Operations as described for portions 310 and 314 for FIG. 19 are substantially the same. SIT from portion 306 is received by a second lens (not shown) and transmitted a second image sensor (not shown) that can be monochromatic. Light source 318A can be broadband (emit S1/S2/S3). The second sensor generates data 324 for generating image 332. For example, to implement two-channel operation for portions 306 and 310 only, S2T from portion 314 is received by a second lens (not shown) and transmitted a second image sensor (not shown) that can be monochromatic. Light source 318B can be broadband (emit S1/S2/S3). The second sensor generates data 328 for generating image 336. Operations as described for portions 306 and 310 for FIG. 19 are substantially the same. It should be understood that other configurations of components in system 600 are possible to implement two-channel optical imaging. In an example embodiment, two-channel imaging is performed for only two of portions 306, 310, or 314 and imaging is not performed on the remaining portion 306, 310, or 314. That is, a second lens and image sensor are not employed to image the remaining portion 306, 310, or 314.

For the sake of brevity, portions of the following discussion are directed to system 300 in FIG. 16; however, it should be understood that the discussion is applicable to FIGS. 17 through 19 as well. Further, the following discussion is directed to embodiments in which multiple channel optical sensing is implemented for all three of portions 306, 310, and 314. However, it should be understood that the discussion is applicable to the two-channel embodiments discussed above. Using a single lens, such as lens 320, and image sensor, such as sensor 322, in place of three lens and sensors, reduces cost and complexity of system 300. All three spectrums S1, S2, and S3, transmitted by lens 320 are received simultaneously by single image sensor 322. However, if sensor 322 is a monochrome sensor, conventional signal processing cannot be used to generate images 332, 334, and 346. For example, a monochrome sensor cannot distinguish among the red, blue, and green and cannot use conventional signal processing to separate spectrums S1T, S2T, and S3T to generate images 332, 334, and 346. Advantageously, system 300 uses a color imaging sensor for sensor 322, which is able to distinguish among spectrums S1T, S2T, and S3T.

Since a single, separate, respective color from the red, blue, and green spectrums is used for each of spectrums S1T, S2T, and S3T, imager 322 is able to transmit data 324, 326, and 328 for single respective spectrums and hence, a single respective image of each of portions 306, 310, or 314 can be generated using conventional signal processing operations. For example, spectrums S1T, S2T, and S3T can consist of red, blue, and green spectrum light, respectively. The red-responsive pixels of the sensor pick up spectrum S1T, the blue-responsive pixels of the sensor pick up spectrum S2T, and the green-responsive pixels of the sensor pick up spectrum S3T.

Thus, the red-responsive pixels record an image of drop 338, the blue-responsive pixels record an image of meniscus 342, and the green-responsive pixels record an image of portion 310. Thus, each group of responsive pixels (for example, the red-responsive pixels) remain unresponsive to, in essence filtering out, images from the other images corresponding to the remaining groups of responsive pixels (for example, the blue and green-responsive pixels). Thus, there is no overlap of spectrums or images included in data transmitted to processor 330 and conventional signal processing can be used to generate images 332, 334, and 346.

The use of broad-band reflecting mirrors/reflecting operations rather than color filtering reflecting and transmitting can reduce the cost of respective optics systems 319 in FIGS. 17 through 19.

In an example embodiment (not shown), a single lens, such as lens 320, and a single monochrome image sensor are used in a time multiplexing arrangement in an infusion pump. For example, using FIG. 19 as a reference, each of light sources 318A/B/C emits the same spectrum of light. The emitted light is transmitted through portions of an infusion tube, such as infusion tube 302, analogous to portions 306, 310, and 314 described supra. Via an arrangement similar to mirrors 346A/346B and beam combiner 348A, the light, transmitted through the analogous portions, is transmitted to the single lens, which transmits the light to a processor, such as processor 330. As noted above, a monochrome sensor cannot distinguish, using conventional signal processing, three simultaneously received images. However, in the example embodiment, the three light sources are sequentially energized such that only one light source is energized per image frame of the image sensor. For example, in a first frame, the light source emitting light transmitted through the portion analogous to portion 306 is energized, in the next frame, the light source emitting light transmitted through the portion analogous to portion 310 is energized, and in the next frame the light source emitting light transmitted through the portion analogous to portion 314 is energized. The processor receives only one image per frame and is able to transmit respective data for each image in each frame to the processor. The processor in turn is able to generate separate images for each of the analogous portions of the pump. The use of a monochrome image sensor and three backlights emitting the same spectrum reduces the cost of the pump in the example embodiment.

The following discussion provides further detail regarding FIGS. 16 through 19. It should be understood that the following discussion is applicable to the two-channel embodiments discussed above. In an example embodiment, lens elements (not shown) can be added to respective image paths (paths traversed by light from a light source to an image sensor) for systems 300 through 600 to compensate for unequal image paths. In an example embodiment, a spectrum of light in the near infra red range (for example, between 700 nm and 1,000 nm) can be used to illuminate portions 306, 310, or 314. In an example embodiment, light source 318 and/or light sources 318A/B/C are LEDs and the LEDs are pulsed to improve operating efficiency or create a strobe effect which eliminates motion blur of moving artifacts. The pulsing is synchronized with the shutter speed of image sensor 322. In an example embodiment, the general configuration of FIG. 18, which does not use a beam combiner, is modified by using three light sources as shown in FIG. 19. The resulting combination uses fewer mirrors than shown in FIG. 18, reducing the cost of the embodiment.

Thus, it is seen that the objects of the invention are efficiently obtained, although changes and modifications to the invention should be readily apparent to those having ordinary skill in the art, without departing from the spirit or scope of the invention as claimed. Although the invention is described by reference to a specific preferred embodiment, it is clear that variations can be made without departing from the scope or spirit of the invention as claimed.

What is claimed is:

1. An optical imaging system for use with an infusion tube, the optical imaging system comprising:
    a first portion disposed near one end of a target object;
    a second portion disposed near an opposite end of the target object;
    a third portion disposed between the first and second portions;
    at least one light source for emitting at least two of a first spectrum of light, a second spectrum of light, or a third spectrum of light;
    an optics system including:
    a single lens receiving and transmitting at least two of: the first spectrum of light transmitted through only the first portion; the second spectrum of light transmitted through only the second portion; or, the third spectrum of light transmitted through only the third portion;
    a single color image sensor for: receiving the at least two of the first, second, or third spectrums of light from the single lens; and, generating and transmitting data characterizing the at least two of the first, second, or third spectrums of light received from the single lens;
    a memory element for storing computer executable instructions; and,
    at least one processor which executes the computer executable instructions and generates, using the data, at least two of first, second, or third images of the corresponding first, second, and third portions, respectively, wherein the at least one processor presents the at least two of first, second, or third images that are distinguishable based on the at least two of first, second, or third spectrums of light,
    wherein the first portion includes a drop pendant and the first image includes an image of the drop pendant; the at least one processor is configured to determine a volume of the drop pendant using the first image; the third portion includes a meniscus for fluid and the third image includes an image of the meniscus; and, the at least one processor configured to execute the computer executable instructions to determine a position of the meniscus using the third image.

2. The optical imaging system of claim 1, wherein the single image sensor consists of a single color image sensor.

3. The optical imaging system of claim 1, wherein the at least one light source consists of a single light source.

4. The optical imaging system of claim 1, wherein the at least one light source includes a plurality of light sources.

5. The optical imaging system of claim 1, wherein the at least one light source includes three light sources.

6. The optical imaging system of claim 1, wherein an air bubble is present in the second portion and the second image includes an image of the air bubble.

7. The optical imaging system of claim 6, the at least one processor configured to execute the computer executable instructions to determine a volume of the air bubble using the second image.

8. The optical imaging system of claim 1, wherein: the at least one light source emits at least two of red, blue, and green spectrum light; the first spectrum of light consists of one of the red, blue, or green spectrum light; the second spectrum of light consists of one of the red, blue, or green spectrum light not included in the first spectrum; and, the third spectrum of light consists of one of the red, blue, or green spectrums of light not included in the first or second spectrums of light.

9. The optical imaging system of claim 1, wherein the optics system includes a mirror for reflecting one only of the first, second, or third spectrums of light transmitted by the first, second, or third portions, respectively.

10. The optical imaging system of claim 1, wherein the optics system includes: a first mirror for reflecting one only of the first, second, or third spectrums of light transmitted by the first, second, or third portions, respectively; and, a second mirror for reflecting another only of the first, second, or third spectrums of light transmitted by the first, second, or third portions, respectively.

11. The optical imaging system of claim 1, wherein the optics system includes a beam combiner for reflecting two only of the first, second, or third spectrums of light transmitted by the first, second, or third portions, respectively.

12. The optical imaging system of claim 1, wherein the optics system includes a mirror for: transmitting to one of the first, second, or third portions, one only of the first, second, or third spectrums of light emitted by the at least one light source; or, reflecting to one of the first, second, or third portions, one only of the first, second, or third spectrums of light emitted by the at least one light source.

13. An optical imaging system for use with an infusion tube, the optical imaging system comprising:
a first portion disposed near one end of a target object;
a second portion disposed near an opposite end of the target object;
a third portion disposed between the first and second portions;
a single light source for emitting a first spectrum of light, a second spectrum of light, or a third spectrum of light;
an optics system including:
a single lens receiving and transmitting at least two of: the first spectrum of light transmitted through only the first portion; the second spectrum of light transmitted through only the second portion; and, the third spectrum of light transmitted through only the third portion;
a single color image sensor for: receiving the at least two of the first, second, or third spectrums of light from the single lens; and, generating and transmitting data characterizing the at least two of the first, second, or third spectrums of light received from the single lens;
a memory element for storing computer executable instructions; and,
at least one processor which executes the computer executable instructions and generates, using the data, at least two of first, second, or third images of the corresponding first, second, and third portions, respectively, wherein the at least one processor presents the at least two of first, second, or third images that are distinguishable based on the at least two of first, second, or third spectrums of light,
wherein the first portion includes a drop pendant and the first image includes an image of the drop pendant; the at least one processor is configured to determine a volume of the drop pendant using the first image; the third portion includes a meniscus for fluid and the third image includes an image of the meniscus; and, the at least one processor configured to execute the computer executable instructions to determine a position of the meniscus using the third image.

14. The optical imaging system of claim 13, wherein the optics system includes: a first mirror for reflecting one only of the first, second, or third spectrums of light transmitted by the first, second, or third portions, respectively; and, a second mirror for reflecting another only of the first, second, or third spectrums of light transmitted by the first, second, or third portions, respectively.

15. The optical imaging system of claim 13, wherein the optics system includes a beam combiner for reflecting two only of the first, second, or third spectrums of light transmitted by the first, second, or third portions, respectively.

16. An optical imaging system for use with an infusion tube, the optical imaging system comprising:
a first portion disposed near one end of a target object;
a second portion disposed near an opposite end of the target object;
a third portion disposed between the first and second portions;
at least one of: a first light source for emitting a first spectrum of light only; a second light source for emitting a second spectrum of light only; or, a third source of light for emitting a third spectrum of light only;
an optics system including:
a single lens receiving and transmitting at least one of: the first spectrum of light transmitted through only the first portion; the second spectrum of light transmitted through only the second portion; or, the third spectrum of light transmitted through only the third portion;
a single color image sensor for: receiving the at least one of the first, second, or third spectrums of light from the single lens; and, generating and transmitting data characterizing the at least one of the first, second, or third spectrums of light received from the single lens;
a memory element for storing computer executable instructions; and,
at least one processor which executes the computer executable instructions and generates, using the data, at least one of first, second, or third images of the corresponding first, second, and third portions, respectively, wherein: the first, second, and third spectrums of light are free of overlapping wavelengths amongst each other, and the at least one processor presents the at least one of first, second, or third images that are distinguishable based on the at least one of first, second, or third spectrums of light,
wherein the first portion includes a drop pendant and the first image includes an image of the drop pendant; the at least one processor is configured to determine a volume of the drop pendant using the first image; the third portion includes a meniscus for fluid and the third image includes an image of the meniscus; and, the at least one processor configured to execute the computer executable instructions to determine a position of the meniscus using the third image.

17. The optical imaging system of claim 16, wherein the optics system includes: a first mirror for reflecting only one of the first, second, or third spectrums of light transmitted by the first, second, or third portions, respectively; and, a second mirror for reflecting another one of the first, second, or third spectrums of light transmitted by the first, second, or third portions, respectively.

18. The optical imaging system of claim 16, wherein the optics system includes a beam combiner for reflecting two only of the first, second, or third spectrums of light transmitted by the first, second, or third portions, respectively.

19. A method of imaging an infusion tube, comprising:
disposing a first portion near one end of a target object;
disposing a second portion near an opposite end of the target object;
disposing a third portion between the first and second portions;
storing, in a memory element, computer executable instructions;
emitting at least two of a first spectrum of light, a second spectrum of light, or a third spectrum of light from at least one light source;
receiving and transmitting, using a single lens at least two of: the first spectrum of light transmitted through only the first portion; the second spectrum of light transmitted through only the second portion; or, the third spectrum of light transmitted through only the third portion;
receiving, using a single color image sensor, the at least two of the first, second, or third spectrums of light from the single lens;
generating and transmitting, using the single image sensor, data characterizing the at least two of the first, second, or third spectrums of light received from the single lens; and,
executing, using the at least one processor, the computer executable instructions to generate, using the data, at least two of first, second, or third images of the corresponding first, second, and third portions, respectively, wherein the at least one processor presents the at least two of first, second, or third images that are distinguishable based on the at least two of first, second, or third spectrums of light.

20. The method of claim 19, wherein the single image sensor consists of a single color image sensor.

21. The method of claim 19, wherein the at least one light source consists of a single light source.

22. The method of claim 19, wherein the at least one light source includes a plurality of light sources.

23. The method of claim 19, wherein the at least one light source includes three light sources.

24. The method of claim 19, wherein: the first portion includes a drop pendant from the drip tube and the first image includes an image of the drop; and, the third portion includes a meniscus for fluid in the drip chamber and the third image includes an image of the meniscus; and, the method further comprising executing, using the at least one processor, the computer executable instructions to: determine, using the first image, a volume of the pendant drop using the first image; and, determining, using the third image, a position of the meniscus using the third image.

25. The method of claim 19, wherein an air bubble is present in the second portion and the second image includes an image of the air bubble.

26. The method of claim 19, further comprising executing, using the at least one processor, the computer executable instructions to determine, using the second image, a volume of the air bubble.

27. The method of claim 19, wherein: emitting at least two of the first, second, or third spectrums of light includes emitting at least two of red, blue, or green spectrum light; the first spectrum of light consists of one of the red, blue, or green spectrum light; the second spectrum of light consists of one of the red, blue, or green spectrum light not included in the first spectrum; and, the third spectrum of light consists of one of the red, blue, or green spectrums of light not included in the first or second spectrums of light.

28. The method of claim 19, further comprising reflecting, using a mirror, one only of the first, second, or third spectrums of light transmitted by the first, second, or third portions, respectively.

29. The method of claim 19, further comprising: reflecting, using a first mirror, one only of the first, second, or third spectrums of light transmitted by the first, second, or third portions, respectively; and, reflecting, using a second mirror, another only of the first, second, or third spectrums of light transmitted by the first, second, or third portions, respectively.

30. The method of claim 19, further comprising reflecting, using a beam combiner, two only of the first, second, or third spectrums of light transmitted by the first, second, or third portions, respectively.

31. The method of claim 19, further comprising: transmitting, using a mirror, to one of the first, second, or third portions, one only of the first, second, or third spectrums of light emitted by the at least one light source; or, reflecting, using a mirror, to one of the first, second, or third portions, one only of the first, second, or third spectrums of light emitted by the at least one light source.

32. A method of imaging an infusion tube, comprising:
disposing a first portion near one end of a target object;
disposing a second portion near an opposite end of the target object;
disposing a third portion between the first and second portions;
storing computer executable instructions in a memory element;
emitting, using a single light source, at least two of: a first spectrum of light, a second spectrum of light, or a third spectrum of light;
receiving and transmitting, using a single lens, at least two of: the first spectrum of light transmitted through only the first portion; the second spectrum of light transmitted through only the second portion; or, the third spectrum of light transmitted through only the third portion;
receiving, using a single color image sensor, the at least two of the first, second, or third spectrums of light from the single lens;
generating and transmitting, using a single color image sensor, data characterizing the at least two of the first, second, or third spectrums of light received from the single lens; and,
executing, using at least one processor, the computer executable instructions to generate, using the data, at least two of first, second, or third images of the corresponding first, second, and third portions, respectively, wherein the at least one processor presents the at least two of first, second, or third images that are distinguishable based on the at least two of first, second, or third spectrums of light, wherein the first portion includes a drop pendant and the first image includes an image of the drop pendant; the at least one processor is configured to determine a volume of the drop pendant using the first image; the third portion includes a meniscus for fluid and the third image includes an image of the meniscus; and, the at least one processor configured to execute the computer executable instructions to determine a position of the meniscus using the third image.

33. The method of claim 32, further comprising: reflecting, using a first mirror, one only of the first, second, or third spectrums of light transmitted by the first, second, or third portions, respectively; and, reflecting, using a second mirror, another only of the first, second, or third spectrums of light transmitted by the first, second, or third portions, respectively.

34. The method of claim 32, further comprising reflecting, using a beam combiner, two only of the first, second, or third spectrums of light transmitted by the first, second, or third portions, respectively.

35. A method of imaging an infusion tube, comprising:

disposing a first portion near one end of a target object;

disposing a second portion near an opposite end of the target object;

disposing a third portion between the first and second portions;

storing computer executable instructions in a memory element;

emitting at least one of: a first spectrum of light only using a first light source; a second spectrum of light only using a second light source; or, a third spectrum of light only using a third light source;

receiving and transmitting, using a single lens, at least one of: the first spectrum of light transmitted through only the first portion; the second spectrum of light transmitted through only the second portion; or, the third spectrum of light transmitted through only the third portion;

receiving, using a single color image sensor, the at least one of the first, second, or third spectrums of light from the single lens;

generating and transmitting, using the single color image sensor, data characterizing the at least one of the first, second, or third spectrums of light received from the single lens; and, executing, using at least one processor, the computer executable instructions to generate, using the data, at least one of first, second, or third images of the corresponding first, second, or third portions, respectively, wherein the first, second, and third spectrums of light are free of overlapping wavelengths amongst each other, and the at least one processor presents the at least one of first, second, or third images that are distinguishable based on the at least one of first, second, or third spectrums of light, wherein the first portion includes a drop pendant and the first image includes an image of the drop pendant; the at least one processor is configured to determine a volume of the drop pendant using the first image; the third portion includes a meniscus for fluid and the third image includes an image of the meniscus; and, the at least one processor configured to execute the computer executable instructions to determine a position of the meniscus using the third image.

36. The method of claim 35 further comprising: reflecting, using a first mirror, one only of the first, second, or third spectrums of light transmitted by the first, second, or third portions, respectively; and, reflecting, using a second mirror, another one only of the first, second, or third spectrums of light transmitted by the first, second, or third portions, respectively.

37. The method of claim 35, further comprising reflecting, using a beam combiner, two only of the first, second, or third spectrums of light transmitted by the first, second, or third portions, respectively.

* * * * *